United States Patent
Debad et al.

(10) Patent No.: US 9,804,173 B2
(45) Date of Patent: Oct. 31, 2017

(54) MULTIPLEXED ASSAY KIT TO EVALUATE THE EFFICACY OF TREATMENT FOR INFLAMMATORY BOWEL DISEASE

(71) Applicant: Meso Scale Technologies, LLC, Rockville, MD (US)

(72) Inventors: Jeff D. Debad, Gaithersburg, MD (US); Eli N. Glezer, Del Mar, CA (US); Sudeep M. Kumar, Gaithersburg, MD (US)

(73) Assignee: MESO SCALE TECHNOLOGIES, LLC, Rockville, MD (US)

( * ) Notice: Subject to any disclaimer, the term of this patent is extended or adjusted under 35 U.S.C. 154(b) by 0 days.

(21) Appl. No.: 14/478,221

(22) Filed: Sep. 5, 2014

(65) Prior Publication Data

US 2014/0378347 A1    Dec. 25, 2014

Related U.S. Application Data

(60) Continuation of application No. 13/775,952, filed on Feb. 25, 2013, now abandoned, which is a division of application No. 12/818,093, filed on Jun. 17, 2010, now abandoned, which is a continuation of application No. 11/301,274, filed on Dec. 9, 2005, now abandoned.

(60) Provisional application No. 60/634,590, filed on Dec. 9, 2004.

(51) Int. Cl.
*G01N 33/68* (2006.01)

(52) U.S. Cl.
CPC ..... *G01N 33/6893* (2013.01); *G01N 33/6863* (2013.01); *G01N 2333/523* (2013.01); *G01N 2333/525* (2013.01); *G01N 2333/70578* (2013.01); *G01N 2800/065* (2013.01); *G01N 2800/52* (2013.01)

(58) Field of Classification Search
CPC ........... G01N 33/6863; G01N 33/6893; G01N 2333/523; G01N 2333/525; G01N 2333/70578; G01N 2800/065; G01N 2800/52
See application file for complete search history.

(56) References Cited

U.S. PATENT DOCUMENTS

| | | | |
|---|---|---|---|
| 4,168,146 A | 9/1979 | Grubb et al. | |
| 4,235,601 A | 11/1980 | Deutsch et al. | |
| 4,366,241 A | 12/1982 | Tom et al. | |
| 4,442,204 A | 4/1984 | Greenquist et al. | |
| 5,028,535 A | 7/1991 | Buechler et al. | |
| 5,582,998 A | 12/1996 | Adolf | |
| 6,297,015 B1 | 10/2001 | Shafran | |
| 6,977,722 B2 | 12/2005 | Wohlstadter et al. | |
| 7,063,946 B2 | 6/2006 | Kenten et al. | |
| 7,497,997 B2 | 3/2009 | Glezer et al. | |
| 2003/0099635 A1* | 5/2003 | Barstow et al. ........... 424/130.1 | |
| 2003/0113713 A1 | 6/2003 | Glezer et al. | |
| 2003/0207290 A1 | 11/2003 | Kenten et al. | |
| 2004/0022677 A1 | 2/2004 | Wohlstadter et al. | |
| 2004/0121350 A1 | 6/2004 | Anderberg et al. | |
| 2004/0126767 A1 | 7/2004 | Anderberg et al. | |
| 2004/0189311 A1 | 9/2004 | Glezer et al. | |
| 2004/0253637 A1 | 12/2004 | Buechler et al. | |
| 2005/0052646 A1 | 3/2005 | Wohlstadter et al. | |
| 2005/0142033 A1 | 6/2005 | Glezer et al. | |
| 2006/0205012 A1 | 9/2006 | Debad et al. | |
| 2010/0316992 A1 | 12/2010 | Debad et al. | |
| 2013/0172431 A1 | 7/2013 | Debad et al. | |

FOREIGN PATENT DOCUMENTS

WO    2004/058055 A2    7/2004

OTHER PUBLICATIONS

Stratagene Catalog. p. 39, 1988.*
Mazzucchelli L, et al. J. Pathology. 18:201-206, 1996.*
Grimm MC and Doe WF. Inflammatory Bowel Diseases. 2:88-96, 1996.*
Noguchi M, et al. 43:203-209, 1998.*
Andreakos E. et al., "Is Targeting Toll-Like Receptors and their Signaling Pathway a Useful Therapeutic Approach to Modulating Cytokine-Driven Inflammation?", Immunological Reviews 202:202-265 (2004).
Cominelli F., "Cytokine-Based Therapies for Crohn's Disease-New Paradigms", N. Engl. J. Med. 351:2045-2048 (2004).
Grip O. et al., "Circulating Monocytes and Plasma Inflammatory Biomarkers in Active Crohn's Disease", Inflamm. Bowel Dis. 10(3):193-200 (2004).
Gustot T. et al., "In Vivo Regulation of Soluble Cytokine-Receptors by Infliximab and Steroids in Crohn's Disease", Gastroenterology 126(4):A567 (2004).
Hanai H. et al., "Correlation of Serum Soluble TNF-Alpha Receptors I and II Levels with Disease Activity in Patients with Ulcerative Colitis", Amer. J. Gastroenterology 99(8):1532-1538 (2004).
Kitamura K. et al., "Pivotal Roles of Interleukin-6 in Transmural Inflammation in Murine T Cell Transfer Colitis", J. Leukocyte Biol. 76:1-7 (2004).
Lindsay J.O. et al., "IL-10 Gene Therapy is Therapeutic for Dextran Sodium Sulfate-Induced Murine Colitis", Dig. Dis. Sci. 49(7-8):1327-1334 (2004).

(Continued)

*Primary Examiner* — Robert Landsman
(74) *Attorney, Agent, or Firm* — Scully, Scott, Murphy & Presser, P.C.

(57) ABSTRACT

Disclosed are methods for conducting diagnostic tests for the detection of the inflammatory bowel diseases, such as Crohn's disease and ulcerative colitis. Also described are methods for monitoring a patient by administering tests of the present invention. Also described are methods for monitoring patient's treatment by administering tests of the present invention. Also described are methods for evaluating the effectiveness of a drug or a drug candidate by administering tests of the present invention to samples from patients, animal models, and cell cultures treated with a drug or a drug candidate. Also disclosed are methods for determining the usefulness of analytes, e.g. cytokines, for acting as diagnostic and monitoring markers for inflammatory bowel disease in the various methods of the invention.

19 Claims, 16 Drawing Sheets

(56) References Cited

OTHER PUBLICATIONS

Liotta L.A. et al., "High-Resolution Serum Proteomic Patterns for Ovarian Cancer Detection", Endocrine-Related Cancer 11:585-587 (2004).
Mannon P.J. et al., "Anti-Interleukin-12 Antibody for Active Crohn's Disease", N. Engl. J. Med. 351:2069-2079 (2004).
Nishimoto et al., "Inhibition of IL-6R for Treatment of Inflammatory Diseases", Curr. Op. Pharmacology 4:386-391 (2004).
Spoettl T. et al., "Identification and Quantification of Soluble TNF Receptors I and II in Serum of IBD Patients", Digestive Disease Week Abstracts and Itinerary Planner Page Abstract No. M1238 (2003).
Banks C. et al., Chemokine Expression in IBD. Mucosal Chemokine Expression is Unselectively Increased in Both Ulcerative Colitis and Crohn's Disease, J. Pathol. 199(1):28-35 (2003).
Holtmann M.H. et al., "Tumor Necrosis Factor-Receptor 2 is Up-Regulated on Lamina Propria T Cells in Crohn's Disease and Promotes Experimental Colitis In Vivo", Eur. J. Immunol. 32(11):3142-3151 (2002).
Mir A. et al., "Elevated Serum Eotaxin Levels in Patients with Inflammatory Bowel Disease", Am. J. Gastroenterology 97(6):1452-1457 (2002).
Mizoguchi E. et al., "Role of Tumor Necrosis Factor Receptor 2 (TNFR2) in Colonic Epithelial Hyperplasia and Chronic Intestinal Inflammation in Mice", Gastroenterology 122(1):134-144 (2002).
Petricoin E.F. et al., "Use of Proteomic Patterns in Serum to Identify Ovarian Cancer", Lancet 359:572-577 (2002).
McCormack G. et al., "Tissue Cytokine and Chemokine Expression in Inflammatory Bowel Disease", Inflamm. Res. 50(10):491-495 (2001).
Indaram A.V. et al., "Mucosal Cytokine Production in Radiation-Induced Proctosigmoiditis Compared with Inflammatory Bowel Disease", Am. J. Gastroenterology 95(5):1221-1225 (2000).
Nielsen O. et al., "Established and Emerging Biological Activity Markers of Inflammatory Bowel Disease", Amer. J. of Gastroenterology 95(2):359-367 (2000).
Park M.K. et al., "A Latex Bead-Based Flow Cytometric Immunoassay Capable of Simultaneous Typing of Multiple Pneumococcal Serotypes (Multibead Assay)", Clin. Diagn. Lab Immunol. 7:486-489 (2000).
Vignali D., "Multiplexed Particle-Based Flow Cytometric Assays", J. Immunol. Meth. 243:243-255 (2000).
Chen R. et al., "Simultaneous Quantification of Six Human Cytokines in a Single Sample Using Microparticle-Based Flow Cytometric Technology", Clin. Chem. 45:1693-1694 (1999).
Boyd, Professional Practice in Clinical Chemistry: A Companion Text, Chapter 2: Reference Limits in the Clinical Laboratory. D.R. Dufour, Ed., Washington D.C.: American Assoc. Clin. Chem. 2-1 - 2-7. 4 pages (1999).
Boyd, Professional Practice in Clinical Chemistry: A Companion Text, Chapter 3: Statistical Aids for Test Interpretation. D.R. Dufour, Ed., Washington, D.C.: American Assoc. Clin. Chem. 3-1-3-11. 6 pages (1999).
Uguccioni M. et al., "Increased Expression of IP-10, IL-8, MCP-1, and MCP-3 in Ulcerative Colitis", Amer. J. Pathol. 155(2):331-336 (1999).
Rogler G. et al., "Cytokines in Inflammatory Bowel Disease", Wolrd J. Surg. 22(4):382-389 (1998).
Kmiec Z., "Cytokines in Inflammatory Bowel Disease", Arch. Immunol. Ther. Exp. (Warsz) 46(3):143-155 (1998), Abstract only.
Noguchi M. et al., "Secretion Imbalance Between Tumour Necrosis Factor and its Inhibitor in Inflammatory Bowel Disease", Gut 43(2):203-209 (1998).
Dieleman L.A. et al., "Kinetics of Cytokine Expression During Healing of Acute Colitis in Mice", Am. J. Physiol. 271 (1):G130-G136 (1996).
Stokkers P.C.F. et al., "Tumor Necrosis Factor (TNF) in Inflammatory Bowel Disease: Gene Polymorphisms, Animal Models, and Potential for Anti-TNF Therapy", J. Inflammation 47:97-103 (1996).
Hadziselimovic F. et al., "Soluble Tumour Necrosis Factor Receptors P55 and P75 in the Urine Monitor Disease Activity and the Efficacy of Treatment of Inflammatory Bowel Disease", Gut. 37(2):260-263 (1995).
Murtaugh P.A., "ROC Curves with Multiple Marker Measurements", Biometrics 51:1514-1522 (1995).
Zweig M.H. et al., "Receiver-Operating Characteristic (ROC) Plots: A Fundamental Evaluation Tool in Clinical Medicine", Clin. Chem. 39(4):561-577 (1993).
International Preliminary Report on Patentability for corresponding International Application No. PCT/US2005/044803, dated Jun. 13, 2007.
International Search Report for corresponding International Application No. PCT/US2005/044803, dated Oct. 17, 2006.
Final Office Action dated Aug. 12, 2013 received in related U.S. Appl. No. 13/775,952.
Final Office Action dated Dec. 18, 2009 received in related U.S. Appl. No. 11/301,274.
Office Action dated Jan. 23, 2009 received in related U.S. Appl. No. 11/301,274.
Office Action dated Feb. 26, 2008 received in related U.S. Appl. No. 11/301,274.
Office Action dated Jul. 3, 2012 received in related U.S. Appl. No. 12/818,093.

* cited by examiner

MULTIPLEXED ASSAY KIT TO EVALUATE THE EFFICACY OF TREATMENT FOR INFLAMMATORY BOWEL DISEASE

CROSS REFERENCES TO RELATED APPLICATIONS

This is a divisional of U.S. application Ser. No. 12/818,093, filed Jun. 17, 2010, which is now abandoned, which is a continuation of U.S. application Ser. No. 11/301,274, filed Dec. 9, 2005, which is now abandoned, and which claims priority to U.S. Provisional Application No. 60/634,590, filed Dec. 9, 2004, each of which is incorporated herein by reference in its entirety. This application is a continuation of U.S. application Ser. No. 13/775,952, filed Feb. 25, 2013, which is a divisional of U.S. application Ser. No. 12/818,093, filed Jun. 17, 2010, which is now abandoned, which is a continuation of U.S. application Ser. No. 11/301,274, filed Dec. 9, 2005, which is now abandoned, and which claims priority to U.S. Provisional Application No. 60/634,590, filed Dec. 9, 2004, each of which is incorporated herein by reference in its entirety.

FIELD OF THE INVENTION

This application relates to assay methods, modules, and kits for conducting diagnostic assays for inflammatory diseases.

BACKGROUND OF THE INVENTION

Inflammatory bowel disease (IBD) encompasses a group of diseases such as ulcerative colitis (UC) and Crohn's disease (CD). IBDs can be difficult to diagnose. An initial diagnosis, made on the basis of medical history and physical examination, is generally confirmed via imaging tests to look at the intestines and laboratory culture tests to rule out bacterial, viral and parasitic infections. The conditions may go undiagnosed for years because symptoms usually develop gradually and less than all of the intestines may be involved.

Colonoscopy can be used to image the intestines and colon. A doctor uses a thin, lighted endoscope to look at the entire intestines and distinguish between IBDs on the basis of the location of ulcerations. Crohn's disease affects some areas of the intestines and skips over others. Ulcerative colitis is more indiscriminate. Endoscopy is also used to take a biopsy of intestinal tissue, which can be used to identify the deep inflammation of the bowel that is characteristic of Crohn's disease. X-rays (after oral or rectal ingestion of Barium), computed tomography (CT) scan, and magnetic resonance imaging (MRI) may be helpful in locating fistulas.

A stool analysis (including a test for blood in the stool) is often performed, depending on symptoms, to look for blood and signs of bacterial infection. Blood and urine tests may be done to check for anemia, high white cell counts, or malnutrition—all signs of IBDs.

Currently there is no reliable biochemical test available for IBD. Up-regulation of certain cytokines has been detected in tissue and mucosal samples surgically removed from diseased bowel in IBD patients (Indaram A. V. et al., Mucosal cytokine production in radiation-induced proctosigmoiditis compared with inflammatory bowel disease, *Am J. Gastroenterol.* 2000 95(5):1221-5; McCormack G, et al., Tissue cytokine and chemokine expression in inflammatory bowel disease, *Inflamm Res.* 2001 50(10):491-5). Up-regulation of a membrane-bound cytokine receptor was also observed in diseased bowel tissue from Crohn's patients (Holtmann M. H. et al., Tumor necrosis factor-receptor 2 is up-regulated on lamina propria T cells in Crohn's disease and promotes experimental colitis in vivo, *Eur J Immunol.* 2002 32(11):3142-51). The collection of the tissue and mucosal samples requires the use of invasive and potentially dangerous surgical techniques, thus limiting the practical applicability of these measurements for diagnostics. The diagnostic utility of these measurements is also unknown. In addition, at least one report found that cytokine levels do not discriminate between Crohn's disease and ulcerative colitis (Banks C, et al., Chemokine expression in IBD. Mucosal chemokine expression is unselectively increased in both ulcerative colitis and Crohn's disease, *J. Pathol.* 2003 199 (1):28-35).

Increased levels of IL-1$\beta$, IL-6 and soluble TNF receptor II were observed in stool samples from mice with chemically induced colitis (Lindsay J. O., et al., IL-10 gene therapy is therapeutic for dextran sodium sulfate-induced murine colitis, *Dig Dis Sci.* 2004 49(7-8):1327-34). It is not clear whether similar effects occur in human CD and UC patients.

Up-regulation of cytokine levels in the bowel often does not lead to corresponding changes in blood (Abstract of Kmiec Z., Cytokines in inflammatory bowel disease. *Arch. Immunol. Ther. Exp.* (Warsz). 1998 46(3):143-55). In one study that did report a change in the serum level of a cytokine in IBD, the average serum eotaxin levels for a population of CD and UC patients was shown to be significantly different than the average value calculated for a normal population (Mir A, et al., Elevated serum eotaxin levels in patients with inflammatory bowel disease, *Am J. Gastroenterol.* 2002 June; 97(6):1452-7). No statistical difference was observed between the CD and UC populations. The results showed a significant overlap in the distribution of levels in the normal and diseased population; the serum level of eotaxin would therefore be expected to be a relatively poor predictor of IBD.

SUMMARY OF THE INVENTION

Disclosed herein are inventive assay methods comprising measuring the levels of one or more cytokines in the sample. In some embodiments of the invention, the method may involve determining from measured cytokine levels if the patient has an inflammatory disease and/or determining from measured cytokine levels, the level of inflammation due to an inflammatory disease and/or obtaining and measuring samples at different times to monitor the progression of an inflammatory disease or the effectiveness of treatments for such disease. In one embodiment, the method includes measuring the level of sTNFRII. In certain embodiments, the method includes measuring a plurality of cytokines and may also include comparing the levels of these cytokines to cytokine profiles determined to be indicative of the disease. A variety of samples may be analyzed. In certain embodiments, the samples may be obtained by a non-surgically invasive procedure from a human patient and may, for example, include blood, serum, plasma, fecal, or urine samples.

In some embodiments of the invention, determining the presence or extent of disease may comprise comparing the levels of one or more cytokines to cytokine profiles indicative of the presence or extent of the disease. In one example, the levels of one or more cytokines in blood, serum and plasma samples are compared to cytokine profiles indicative of the presence or extent of the disease. The step of comparing may comprise comparing cytokine levels to detection cut-off values, comparing ratios of cytokine levels to detection cut-off ratio values; comparing levels of two cytokines to detection cut-off lines in correlation plots of the two analytes, comparing levels of multiple cytokines to detection cut-off curves or surfaces in multi-analyte correlation plots and/or comparing levels of multiple cytokines to detection zones (e.g., detection areas or detection volumes) in multi-analyte correlation plots.

One embodiment of the invention includes a method for diagnosing inflammatory bowel disease comprising: measuring the level of sTNFRII in a sample, for example, a sample obtained from a patient suspected of having inflammatory bowel disease; and diagnosing from the measured level the presence or absence in the patient of inflammatory bowel disease. The cytokine (e.g. sTNFRII) level can be measured by a variety of techniques available to a skilled artisan, including binding assay techniques such as immunoassays, solid-phase binding assays and/or agglutination assays. Determination may comprise comparing this measured level to a detection cut-off value, wherein the sTNFRII level above the detection cut-off value is considered indicative of inflammatory bowel disease. In one embodiment, the sample is a blood, serum or plasma sample.

One embodiment of the invention involves a method for diagnosing ulcerative colitis comprising: measuring the level of sTNFRII in a sample, for example, a sample obtained from a patient suspected of having ulcerative colitis; and diagnosing from the measured level the presence or absence in said patient of ulcerative colitis. In one embodiment, the sample is a blood, serum or plasma sample.

In another specific example, the cytokines for diagnosing ulcerative colitis disease comprise one or more cytokines selected from the group consisting of RANTES, sIL-6R, sTNFRII, IL-1β, IL-13, and IL-6. Yet in another specific example, the cytokines for diagnosing ulcerative colitis disease are selected from one or more of the group consisting of RANTES, sIL-6R, sTNFRII, and IL-1β.

In another specific example, the cytokines for diagnosing Crohn's disease comprise one or more cytokines selected from the list consisting of RANTES, sIL-6R, sTNFRII, IL-2, IL-4, IL-5, IL-8, and TNF. In yet another specific example, the cytokines for diagnosing Crohn's disease comprise one or more cytokines selected from the group consisting of RANTES, sIL-6R, and sTNFRII.

Certain embodiments of the methods of the invention may further distinguish ulcerative colitis from Crohn's disease on the basis of the measured level of a selected cytokine, e.g. the measured sTNFRII level. For example, distinguishing ulcerative colitis from Crohn's disease may comprise comparing measured sTNFRII level to a discrimination cut-off value, wherein the measured level below the discrimination cut-off value is considered indicative of Crohn's disease and above the discrimination cut-off value is considered indicative of ulcerative colitis.

In one embodiment of the present invention, the detection cut-off value is set between 5 and 7 ng per ml of sample volume and the discrimination cut-off value is set between 8 and 10 ng per ml of sample volume.

One embodiment of the invention relates to a method for diagnosing inflammatory bowel disease comprising: measuring the level of a first cytokine, for example, in a sample obtained from a patient suspected of having inflammatory bowel disease; measuring the level of one or more additional cytokines, wherein the one or more additional cytokines are different form the first cytokine; and diagnosing from the first cytokine level and from the one or more additional cytokine levels the presence of absence in said patient of inflammatory bowel disease. In one embodiment, the sample is a sample collected via a non-surgically invasive procedure from a patient. In certain cases, the sample comprises a serum, plasma or blood sample. In other cases, the sample comprises a fecal or urine sample.

According to one embodiment of the invention, diagnostically valuable cytokines may be selected from a group comprising IL-1β, IL-12p70, IL-10, IL-2, GM-CSF, TNF, IL-8, IL-4, IL-5, IL-6, Eotaxin, IFN-α, IFN-γ, sIL-6R, IL-12(total), IL-13, MIP-1β, MCP-1, RANTES and sTNFRII. In one specific example, the cytokines are selected from the group consisting of IL-12p70, IL-10, IL-2, TNF, IL-8, IL-4, IL-5, IL-6, Eotaxin, sIL-6R, IL-12(total), MIP-1β, MCP-1, RANTES and sTNFRII. In another specific example, the cytokines are selected from the group consisting of Eotaxin, sIL-6R, MIP-1β, MCP-1, and RANTES. In another specific example, the first cytokine is MCP-1 and the additional cytokine is MIP-1β.

In one embodiment of the invention, sTNFRII is selected as the first cytokine. Thus, the invention is a method for diagnosing inflammatory bowel disease comprising: measuring the sTNFRII level in a sample, for example, a sample obtained from a patient suspected of having inflammatory bowel disease; measuring one or more additional cytokines (e.g., levels of one or more of IL-1β, IL-12p70, IL-10, IL-2, GM-CSF, TNF, IL-8, IL-4, IL-5, IL-6, Eotaxin, IFN-α, IFN-γ, sIL-6R, IL-12(total), IL-13, MIP-1β, MCP-1 and/or RANTES); and diagnosing from the sTNFRII level and from one or more additional cytokine levels the presence or absence of inflammatory bowel disease in the patient. In one specific example, the additional cytokine(s) are selected from the group consisting of one or more of IL-12p70, IL-10, IL-2, TNF, IL-8, IL-4, IL-5, IL-6, Eotaxin, sIL-6R, IL-12(total), MIP-1β, MCP-1 and RANTES. In another specific example, the additional cytokines are selected from the group consisting of one or more of Eotaxin, sIL-6R, MIP-1β, MCP-1, and RANTES. In another specific example, the additional cytokine is MIP-1β.

Determining from the sTNFRII level and from one or more additional cytokine levels if the patient has inflammatory bowel disease may comprise comparing the sTNFRII level and one or more additional levels to a cytokine profile determined to be indicative of inflammatory bowel disease. The step of comparing may comprise comparing cytokine levels to detection cut-off values, comparing ratios of levels to detection cut-off ratio values and/or comparing levels to detection cut-off lines, curves or surfaces in multi-analyte correlation plots. In one embodiment, a sTNFRII level above a sTNFRII detection cut-off value and a level of an additional cytokine below a cytokine detection cut-off value are considered indicative of inflammatory bowel disease. In another embodiment, a ratio of the sTNFRII level to one additional cytokine level above a detection cut-off ratio value is considered indicative of inflammatory bowel disease. In yet another embodiment, a sTNFRII level above a sTNFRII detection cut-off line is considered indicative of inflammatory bowel disease. In yet another embodiment IL-6 is selected as a first cytokine and IL-13 as a second cytokine.

One specific example of the invention also relates to a method for diagnosing inflammatory bowel disease by measuring pair-wise cytokine level profiles selected from the group consisting of sTNFRII/RANTES, sTNFRII/sIL-6R, sIL-6R/RANTES, IL-5/sIL-6R and sTNFRII/IL-4.

According to one embodiment of the invention, the method may comprise distinguishing ulcerative colitis from Crohn's disease for patients having an inflammatory bowel disease on the basis of a measured sTNFRII level and one or more additional measured cytokine levels. In one example, the sTNFRII level and one or more additional cytokine levels are blood, serum or plasma levels. For example, ulcerative colitis can be distinguished from Crohn's disease, according to the invention, by comparing the sTNFRII level and one or more additional cytokine levels to profiles determined to be indicative of Crohn's disease or ulcerative colitis. The step of comparing may comprise comparing levels to discrimination cut-off values, comparing ratios of levels to discrimination cut-off ratio values, and/or comparing levels to discrimination cut-off lines. In one embodiment, ulcerative colitis is distinguished from Crohn's disease by comparing the sTNFRII level to a sTNFRII discrimination cut-off value, wherein a sTNFRII level below said sTNFRII discrimination cut-off value is considered indicative of Crohn's disease and above the sTNFRII discrimination cut-off value is considered indicative of ulcerative colitis. In yet another embodiment, ulcerative colitis is distinguished from Crohn's disease by comparing the sTNFRII level to a sTNFRII discrimination cut-off line, wherein sTNFRII level below the sTNFRII discrimination cut-off line is considered indicative of Crohn's disease and above the sTNFRII discrimination cut-off line is considered indicative of ulcerative colitis.

In yet another embodiment, ulcerative colitis is distinguished from Crohn's disease by comparing a measured sTNFRII level to a cytokine profile defined as areas situated between a first detection cut-off line and a second discrimination cut-off line on a correlation plot.

In one embodiment, ulcerative colitis is distinguished from Crohn's disease by comparing two or more cytokines measured in a patient to a profile of these two or more cytokines, e.g., values, ratios, lines or zones on the correlation plot, indicative of a patient having ulcerative colitis, a patient having Crohn's disease and a healthy individual. In one specific example, pare-wise cytokine profiles are selected from the group consisting of, but not limited to, sTNFRII/RANTES, sTNFRII/sIL-6R, and sTNFRII/IL-4.

Another embodiment of the invention relates to methods for measuring the extent of inflammation due to IBDs. The inventive methods may include an assay method comprising: measuring the level of sTNFRII in a sample, for example, a sample obtained from a patient that has or is suspected to have an inflammatory disease; and determining from the level of sTNFRII the extent of inflammation from the disease.

One embodiment of the invention includes a method comprising: measuring a level of a first cytokine, for example, measuring in a sample obtained from a patient that has or is suspected to have an inflammatory disease; measuring the level of one or more additional cytokines, wherein the one or more additional cytokines differ from the first cytokine; and determining from measured levels the extent of inflammation from the disease. In one embodiment, the cytokines comprise one or more cytokines selected from the group consisting of IL-1β, IL-12p70, IL-10, IL-2, GM-CSF, TNF, IL-8, IL-4, IL-5, IL-6, Eotaxin, IFN-α, IFN-γ, sIL-6R, IL-12(total), IL-13, MIP-1β, MCP-1, RANTES and sTNFRII. In another embodiment, the cytokines are selected from the group consisting of IL-12p70, IL-10, IL-2, TNF, IL-8, IL-4, IL-5, IL-6, Eotaxin, sIL-6R, IL-12(total), MIP-1β, MCP-1, RANTES and sTNFRII. In another embodiment, the cytokines comprise one or more cytokines selected from the group consisting of Eotaxin, sIL-6R, MIP-1β, MCP-1, and RANTES. In another embodiment, the first cytokine is MCP-1 and the second cytokine is MIP-1β.

In yet another embodiment, the first cytokine is sTNFRII. In one specific example of this embodiment, the additional cytokine(s) are selected from the group consisting of IL-12p70, IL-10, IL-2, TNF, IL-8, IL-4, IL-5, IL-6, Eotaxin, sIL-6R, IL-12 (total), MIP-1β, MCP-1 and RANTES. In another specific example, the additional cytokine(s) are selected from the group consisting of Eotaxin, sIL-6R, MIP-1β, MCP-1, and RANTES. In another specific example, the additional cytokine is MIP-1β. In another specific example, a pair of cytokines is selected from the group consisting of, but not limited to, sTNFRII/RANTES, sTNFRII/sIL-6R, and sTNFRII/IL-4.

Another embodiment of the invention relates to methods for monitoring the progression or treatment of IBDs. The invention includes a method for monitoring the progression or treatment of an IBD comprising: measuring the levels of sTNFRII in samples obtained at different times, for example, samples obtained from a patient that has or is suspected to have an inflammatory disease; and determining from the levels of sTNFRII the progression or efficacy of treatment of the disease.

One embodiment of the invention includes a method for monitoring the progression or treatment of an IBD comprising: measuring the levels of a first cytokine in samples obtained at different times, for example, samples obtained from a patient that has or is suspected to have an inflammatory disease; measuring the levels of one or more additional cytokines in the samples from the same patient obtained at the same times as samples for the first cytokine, for example, the same samples, wherein the one or more additional cytokines differ from the first cytokine; and determining from measured levels the progression or efficacy of treatment of the disease. In one embodiment, the cytokines comprise one or more cytokines selected from the group consisting of IL-1β, IL-12p70, IL-10, IL-2, GM-CSF, TNF, IL-8, IL-4, IL-5, IL-6, Eotaxin, IFN-α, IFN-γ, sIL-6R, IL-12(total), IL-13, MIP-1β, MCP-1, RANTES and sTNFRII. In another embodiment, the cytokines comprise one or more cytokines selected from the group consisting of IL-12p70, IL-10, IL-2, TNF, IL-8, IL-4, IL-5, IL-6, Eotaxin, sIL-6R, IL-12 (total), MIP-1β, MCP-1, RANTES and sTNFRII. In another embodiment, the cytokines comprise one or more cytokines selected from the group consisting of Eotaxin, sIL-6R, MIP-1β, MCP-1, and RANTES. In another embodiment, the first cytokine is MCP-1 and the second cytokine is MIP-1β.

In yet another embodiment, the first cytokine is sTNFRII. In one specific example of this embodiment, the additional cytokine(s) are selected from the group consisting of IL-12p70, IL-10, IL-2, TNF, IL-8, IL-4, IL-5, IL-6, Eotaxin, sIL-6R, IL-12 (total), MIP-1β, MCP-1 and RANTES. In another specific example, the additional cytokine(s) are selected from the group consisting of Eotaxin, sIL-6R, MIP-1β, MCP-1, and RANTES. In another specific example, the additional cytokine is MIP-1β. In another specific example, a pair of cytokines is selected from the group consisting of, but not limited to, sTNFRII/RANTES, sTNFRII/sIL-6R, and sTNFRII/IL-4.

Another aspect of the invention involves a method for evaluation of the effectiveness of a drug or drug candidate for treating IBDs. For example, the invention includes a method for evaluating the effectiveness of a drug and/or drug candidate comprising: exposing a human or non-human animal with IBD and/or a model system, for example, a tissue, cell culture or a biochemical system, to the drug or drug candidate; measuring the levels of sTNFRII in a sample obtained from the human or non-human animal or a model system; and determining from the level the effectiveness of the drug or drug candidate.

In another example, the invention includes a method for evaluating the effectiveness of a drug or drug candidate comprising: exposing a human or non-human animal with IBD and/or a model system, for example, a tissue, cell culture or a biochemical system, to the drug or drug candidate; measuring the level of a first cytokine in a sample obtained from the human or non-human animal or a model system; measuring the level of one or more additional cytokines in the same sample or a different sample obtained from the same human or non-human animal or a model system, wherein the one or more additional cytokines differ from the first cytokine; and determining from measured levels the effectiveness of the drug or drug candidate. In one embodiment, the cytokines comprise one or more cytokines selected from the group consisting of IL-1β, IL-12p70, IL-10, IL-2, GM-CSF, TNF, IL-8, IL-4, IL-5, IL-6, Eotaxin, IFN-α, IFN-γ, sIL-6R, IL-12(total), IL-13, MIP-1β, MCP-1, RANTES and sTNFRII. In another embodiment, the cytokines comprise one or more cytokines selected from the group consisting of IL-12p70, IL-10, IL-2, TNF, IL-8, IL-4, IL-5, IL-6, Eotaxin, sIL-6R, IL-12 (total), MIP-1β, MCP-1, RANTES and sTNFRII. In another embodiment, the cytokines comprise one or more cytokines selected from the group consisting of Eotaxin, sIL-6R, MIP-1β, MCP-1, and RANTES. In another embodiment, the first cytokine is MCP-1 and the second cytokine is MIP-1β. In yet another embodiment, the first cytokine is sTNFRII. In one specific example of this embodiment, the additional cytokine(s) are selected from the group consisting of IL-12p70, IL-10, IL-2, TNF, IL-8, IL-4, IL-5, IL-6, Eotaxin, sIL-6R, IL-12(total), MIP-1β, MCP-1 and RANTES. In another specific example, the additional cytokine(s) are selected from the group consisting of Eotaxin, sIL-6R, MIP-1β, MCP-1, and RANTES. In another specific example, the additional cytokine is MIP-1β. In another specific example, a pair of cytokines is selected from the group consisting of, but not limited to, sTNFRII/RANTES, sTNFRII/sIL-6R, and sTNFRII/IL-4.

The method may also include comparing the levels to the levels in a control human or non-human animal that was not treated with the drug or drug candidate. The human or non-human animal in these drug evaluation methods may be replaced with an in vitro IBD model system, for example, tissue, cell culture or biochemical systems that model the behavior of IBDs.

Suitable samples for detecting or monitoring IBD include blood, serum, plasma, fecal matter, biopsy tissue, intestinal mucosa and urine. Advantageously, certain embodiments of the invention allow measurement in samples obtained via non-surgically invasive procedures, such as, for example, blood, serum, plasma, fecal matter, and urine samples. For methods involving the measurement of multiple cytokines, each cytokine may be measured separately. Alternatively, multiplexed measurement approaches (including approaches known in the art such as array-based or flow cytometry-based approaches) may be used to concurrently measure multiple cytokines in a single volume of sample. Such multiplexed measurements may be advantageously carried out in a single assay chamber such as a single test tube, a single well of an assay plate and/or an assay chamber of an assay cartridge.

Certain methods of the invention may be supplemented by conducting a diagnostic test to determine if the patient has viral or bacterial infection. Certain methods of the invention may further comprise administering to the tested patient an effective amount of drug for effective treatment of the diagnosed IBD.

The invention also includes reagents and kits for carrying out the methods of the invention. In one embodiment, a kit comprises antibodies against the cytokines being measured in a method of the invention. The kit may further comprise assay diluents, standards, controls and/or detectable labels. The assay diluents, standards and/or controls may be optimized for a particular sample matrix. For example, for measurements in blood, serum or plasma samples, the diluents, standards and controls may include i) human blood, serum or plasma; ii) animal blood, serum or plasma or iii) artificial blood, serum or plasma substitutes.

A variety of cytokines can potentially be useful as diagnostic marker(s) for performing the inventive methods for the diagnosis and/or monitoring of inflammatory bowel disease and for screening drugs or drug candidates for efficacy in treating inflammatory bowel disease. Indeed, as described in more detail below, certain embodiments of the invention provide methods for determining the efficacy of particular candidate cytokine(s) for acting as such diagnostic marker(s). Using the methods of the present invention, one of ordinary skill in the art will be able to determine without undue experimentation the ability of one or more selected cytokines, including cytokines not specifically listed herein and indeed not yet discovered, to be useful as markers whose measured levels/profiles may be employed in performing the various diagnostic and screening methods of the invention.

BRIEF DESCRIPTION OF DRAWINGS

The accompanying drawings are schematic are not intended to be drawn to scale. In the figures, each identical, or substantially similar, component that is illustrated in various figures is typically represented by a single numeral or notation. For purposes of clarity, not every component is labeled in every figure, nor is every component of each embodiment of the invention shown where illustration is not necessary to allow those of ordinary skill in the art to understand the invention. In the drawings.

DETAILED DESCRIPTION OF THE INVENTION

Figure 1A:
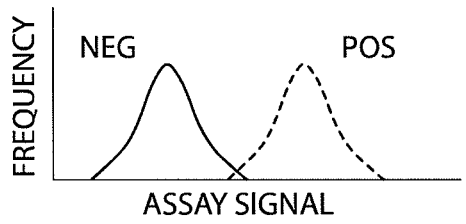
FIGS. 1A-1D depict examples of possible distributions of assay signals for positive and negative samples (FIGS. 1A, 1B, 1C) for an assay and the ROC curves that are generated in each case (FIG. 1D)

Disclosed herein are inventive methods for conducting diagnostic tests for the detection of inflammatory diseases such as inflammatory bowel disease (IBD). The diagnostic tests may comprise measuring analytes in biological samples, for example measuring disease markers, markers of inflammation, and/or cytokines, where the levels of the analytes are indicative of the presence or severity of an inflammatory disease. One aspect of the invention is identifying diagnostically valuable markers of IBDs, for example diagnostically valuable markers of Crohn's disease (CD) and ulcerative colitis (UC). Another aspect of the invention relates to methods for detecting and/or distinguishing various IBDs, such as CD and UC. Another aspect of the invention further relates to methods for monitoring the progression or treatment of inflammatory bowel disease in a patient by administering and/or repetitively administering the diagnostic tests according to the methods of the present invention. In one example, the diagnostic methods may be used to evaluate the effectiveness of a drug or drug candidate for treating inflammatory diseases by measuring the effect of the drug or drug candidate on the levels of disease-specific analytes in samples from patients, animal models, tissue samples and cell cultures treated with a drug or a drug candidate. Another aspect of the invention provides methods for determining the efficacy of particular candidate analytes, such as particular cytokine(s), for acting as diagnostic marker(s) in the inventive methods for the diagnosis and/or monitoring of inflammatory bowel disease and for screening drugs or drug candidates for efficacy in treating inflammatory bowel disease.

Analytes that may be measured using the assay methods of the present invention include inflammatory markers, such as cytokines, secreted proteins that are involved in regulation of immune response. Cytokines include the interleukins (ILs), interferons (IFNs), chemokines, tumor necrosis factors (TNFs), and a variety of colony stimulating factors (CSFs). The term cytokines, as used herein, also includes soluble cytokine receptors. Specific cytokines that may be measured in the assays of the invention include, but are not limited to, cytokines linked to TH1 response, cytokines linked to TH2 response, pro-inflammatory cytokines and/or cytokines selected from the group consisting of IL-1β, IL-12p70, IL-10, IL-2, granulocyte-macrophage colony stimulating factor (GM-CSF), TNF-α, IL-8, IL-4, IL-5, IL-6, Eotaxin, IFN-α, IFN-γ, soluble IL-6 receptor (sIL-6R), IL-12(total), IL-13, MIP-1β, MCP-1, RANTES and soluble TNF-β receptor II (sTNFRII). According to one aspect of the invention, analytes could advantageously measured in a sample obtained via a non-surgically invasive collection technique, such as in a blood, serum, plasma, fecal, or urine sample from a patient having, or suspected to have an IBD.

According to one aspect of the invention, the levels of cytokine or other disease marker candidates are measured in the samples collected from individuals clinically diagnosed with Crohn's disease and ulcerative colitis (e.g., using conventional diagnostic methods, such as doctor's interview, endoscopies, imaging and/or biopsy) and from healthy individuals. Within non-limiting examples of this invention, specific cytokines valuable as a marker for distinguishing between normal and diseased patients could be identified using visual inspection of the data, for example, data plotted on a one-dimensional or multi-dimensional graph, or by using methods of statistical analysis, such as a statistically weighted difference between control individuals and diseased patients and/or Receiver Operating Characteristic (ROC) curve analysis.

For example in one exemplary embodiment of the present invention, diagnostically valuable cytokines may be first identified using a statistically weighted difference between control individuals and diseased patients, calculated as $$\frac{D-N}{\sqrt{\sigma_D * \sigma_N}}$$

where D is the median concentration of a cytokine in patients diagnosed as having, for example, ulcerative colitis or Crohn's disease, N is the median of the control individuals, $\sigma_D$ in the standard deviation of D and $\sigma_N$ is the standard deviation of N. The larger the magnitude, the greater the statistical difference between the diseased and normal populations.

According to one embodiment of the invention, cytokines resulting in a statistically weighted difference between control individuals and diseased patients of greater than 0.2, 0.5, 1, 1.5, 2, 2.5 or 3 could be identified as diagnostically valuable markers.

Another method of statistical analysis that can be useful in the inventive methods of the invention for determining the efficacy of particular candidate analytes, such as particular cytokine(s), for acting as diagnostic marker(s) is Receiver Operating Characteristic (ROC) curve analysis. An ROC curve is a graphical approach to looking at the effect of a cut-off criterion (e.g., a cut-off value for a diagnostic indicator such as an assay signal or the level of an analyte) on the ability of a diagnostic to correctly identify positive and negative samples or subjects. (See, FIGS. 1A-1D) One axis of the ROC curve is the true positive rate (TPR, the probability that a true positive sample/subject will be correctly identified as positive) or, alternatively, the false negative rate (FNR=1−TPR, the probability that a true positive sample/subject will be incorrectly identified as a negative). The other axis is the true negative rate (TNR, the probability that a true negative sample will be correctly identified as a negative) or, alternatively, the false positive rate (FPR=1−TNR, the probability that a true negative sample will be incorrectly identified as positive). The ROC curve is generated using assay results for a population of samples/subjects by varying the diagnostic cut-off value used to identify samples/subjects as positive or negative and plotting calculated values of TPR (or FNR) and TNR (or FPR) for each cut-off value. The area under the curve (referred to herein as the ROC area) is one indication of the ability of the diagnostic to separate positive and negative samples/subjects.

Figure 1B:
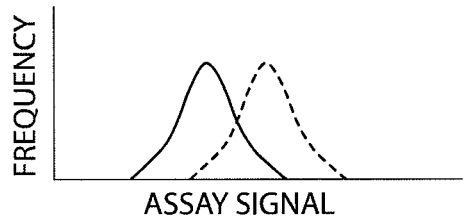
Figure 1C:
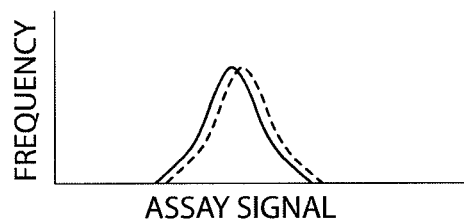
Figure 1D:
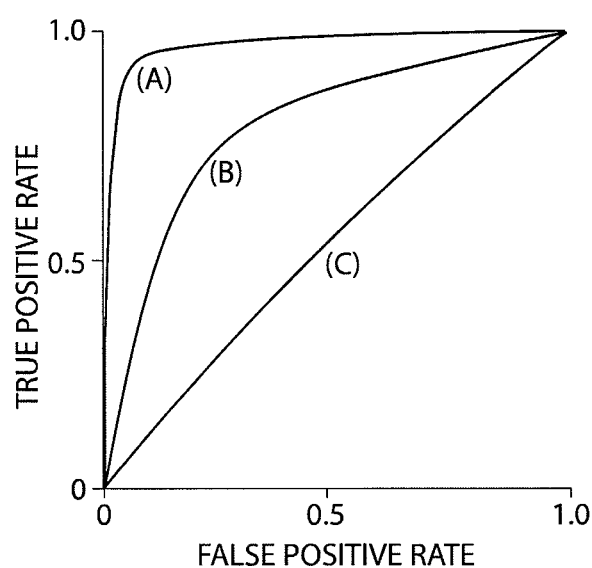
Figure 2A:
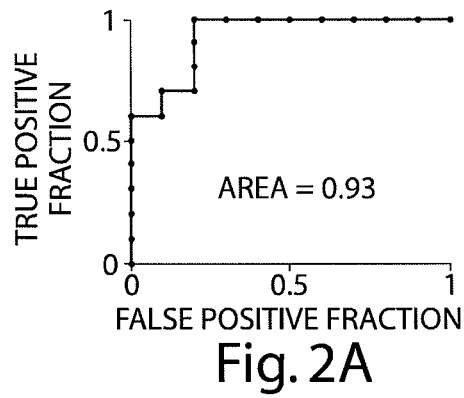
FIGS. 2A-2D depict ROC curves for using sTNFRII for Crohn's disease detection in plasma samples (FIG. 2A), Crohn's disease detection in serum samples (FIG. 2B), ulcerative colitis detection in plasma samples (FIG. 2C), and ulcerative colitis detection in serum samples (FIG. 2D)
Figure 2B:
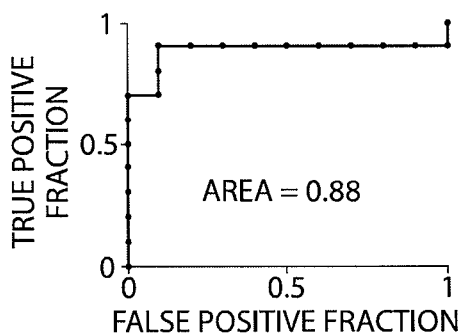
Figure 2C:
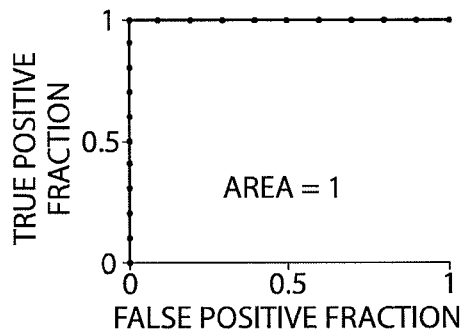
Figure 2D:
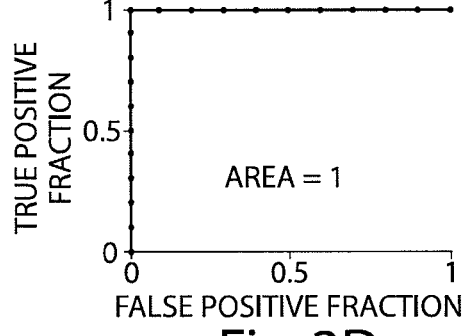

FIGS. 1A-1C show examples of three different distributions of assay signals for positive and negative samples, and FIG. 1D shows the ROC curves that are generated in each case by varying the cut-off value across the range of possible assay signals. A diagnostic assay that almost perfectly separates the negative and positive populations (FIG. 1A) will give an ROC area approaching 1.0. A diagnostic that provides almost no separation of negative and positive populations (FIG. 1C) will give an ROC area approaching 0.5. A diagnostic assay that provides an intermediate level of separation (FIG. 1B) will give an ROC area somewhere in the middle between 0.5 and 1.0. For example, FIGS. 2A-2D depict sTNFRII ROC curves for using TNFRII levels as a diagnostic for Crohn's disease detection using plasma samples (FIG. 2A), Crohn's disease detection using serum samples (FIG. 2B), ulcerative colitis detection using plasma samples (FIG. 2C), and ulcerative colitis detection using serum samples (FIG. 2D).

ROC curve analysis can also provide an approach to selecting a cut-off value that best optimizes the trade-off between TPR and FPR to meet the objectives of a specific application. One approach is to select the cut-off value that maximizes the product of the TPR and TNR, although for certain applications the TPR or TNR may be held more important and weighted more heavily. A more detailed explanation of how ROC analysis can be used to select cut-off values yielding a desired level of statistical confidence for correct diagnosis is presented in MH Zweig, G Campbell, Receiver-operating characteristic (ROC) plots: a fundamental evaluation tool in clinical medicine, *Clin Chem* 1993: 39(4); 561-77; P. A. Murtaugh, ROC curves with multiple marker measurements, *Biometrics* 1995: 51; 1514-22, each of which is incorporated, herein, by this reference.

Diagnostic indicators analyzed by ROC curve analysis may simply be a level of an analyte (e.g., a cytokine) or an assay signal. Alternatively, the diagnostic indicator may be a function of multiple measured values, for example, a function of the level/assay signal of a plurality of analytes (e.g., a plurality of cytokines) or a function that combines the level/assay signal of one or more analytes with a patient scoring value that is determined based on visual, radiological and/or histological evaluation of a patient. The multi-parameter analysis may provide more accurate diagnosis relative to analysis of a single marker.

Candidates for a multi-analyte panel could be selected by using criteria such as individual analyte ROC areas, median difference between groups normalized by geometric interquartile range (IQR) etc. The objective is to partition the analyte space so as to improve separation between groups (for e.g. normal and disease populations) or to minimize the misclassification rate.

One approach is to define a panel response as a weighted combination of individual analytes and then compute an objective function like ROC area, product of sensitivity and specificity etc. See, for e.g., PCT Application No. WO 2004/058055, "Method and System for Disease Detection Using Marker Combinations". The weighting coefficients define the partitioning object; for linear combinations the object is a line in 2 dimensions, a plane in 3 dimensions and a hyperplane in higher dimensions. The optimal coefficients maximize the objective function and can be determined using algorithms for finding function extrema in multiple dimensions—gradient descent methods, downhill simplex methods, simulated annealing and the like; more details can be found in "Numerical Recipes in C, The Art of Scientific Computing", W. Press et al., Cambridge University Press, 1992.

Another approach is to use discriminant analysis, where a multivariate probability distribution (normal, multinomial etc.) is used to describe each group. Several distributions result in partitioning hyperplanes in analyte space. One advantage of this approach is the ability to classify measurements into multiple groups (e.g. normal, disease 1, disease 2) simultaneously, rather than two at a time. For further details, see "Principles of Multivariate Analysis, A User's Perspective", W. J. Krzanowski, Oxford University Press, 2000 and "Multivariate Observations", G. A. F. Seber, John Wiley, 2004. Once the partitioning hyperplanes have been determined, the robustness of different assay panels can be compared by evaluating a distance metric to the separating hyperplanes for each group.

A skilled artisan will readily recognize that because the algorithms described above could be used to find the best classification between groups; they could also be used for distinguishing between different diseases or subgroups of the same disease. Finally, categorical data (age, gender, race etc) can also be coded into different levels and used as an optimizing variable in this process.

One indication (the ROC area) of the diagnostic utility of a selected group of exemplary markers is presented in Table 1.

TABLE 1

| Disease (sample) | Assay | ROC Area |
| --- | --- | --- |
| Crohns (plasma) | RANTES | 0.86 |
| Crohns (serum) | RANTES | 1 |
| Crohns (plasma) | IL-6R | 0.94 |
| Crohns (serum) | IL-6R | 0.87 |
| Crohns (plasma) | TNF-RII | 0.93 |
| Crohns (serum) | TNF-RII | 0.88 |
| Crohns (plasma) | IL-2 | 0.69 |
| Crohns (serum) | IL-2 | 0.76 |
| Crohns (plasma) | IL-4 | 0.7 |
| Crohns (serum) | IL-4 | 0.75 |
| Crohns (plasma) | IL-5 | 0.77 |
| Crohns (serum) | IL-5 | 0.68 |
| Crohns (plasma) | IL-8 | 0.77 |

TABLE 1-continued

| Disease (sample) | Assay | ROC Area |
|---|---|---|
| Crohns (serum) | IL-8 | 0.64 |
| Crohns (plasma) | TNF | 0.58 |
| Crohns (serum) | TNF | 0.77 |
| Crohns (plasma) | MIP-1β | 0.58 |
| Crohns (serum) | MIP-1β | 0.98 |
| Crohns (plasma) | MCP-1 | 0.68 |
| Crohns (serum) | MCP-1 | 0.89 |
| Crohns (plasma) | Eotaxin | 0.56 |
| Crohns (serum) | Eotaxin | 0.78 |
| Crohns (plasma) | IL-1β | 0.91 |
| Crohns (serum) | IL-1β | 0.55 |
| Crohns (plasma) | IFN-γ | 0.79 |
| Crohns (serum) | IFN-γ | 0.55 |
| UC (plasma) | TNF-RII | 1 |
| UC (serum) | TNF-RII | 1 |
| UC (plasma) | IL-6R | 0.93 |
| UC (serum) | IL-6R | 0.87 |
| UC (plasma) | IL-1β | 0.89 |
| UC (serum) | IL-1β | 0.85 |
| UC (plasma) | RANTES | 0.88 |
| UC (serum) | RANTES | 0.97 |
| UC (plasma) | IL-13 | 0.79 |
| UC (serum) | IL-13 | 0.97 |
| UC (plasma) | IL-6 | 0.75 |
| UC (serum) | IL-6 | 0.81 |
| UC (plasma) | MIP-1β | 0.56 |
| UC (serum) | MIP-1β | 0.98 |
| UC (plasma) | MCP-1 | 0.74 |
| UC (serum) | MCP-1 | 0.92 |
| UC (plasma) | Eotaxin | 0.52 |
| UC (serum) | Eotaxin | 0.83 |
| UC (plasma) | IFN-γ | 0.82 |
| UC (serum) | IFN-γ | 0.58 |

According to one embodiment of the invention, cytokines are selected so that the ROC areas exceed, for example, 0.6, 0.7, 0.8 or 0.9. Thus, in one non-limiting example, ulcerative colitis is diagnosed using one or more cytokines selected from the group consisting of RANTES, sIL-6R, sTNFRII, IL-1β, IL-13, IL-6 where the ROC area exceeds 0.6. In yet another specific example, ulcerative colitis is diagnosed using one or more cytokines selected from the group consisting of RANTES, sIL-6R, sTNFRII, IL-1β where the ROC area exceeds 0.8. In another specific example, Crohn's disease is diagnosed using one or more of the cytokines selected from the group consisting of RANTES, sIL-6R, sTNFRII, IL-2, IL-4, IL-5, IL-8, TNF, where the ROC area exceeds 0.6. In yet another specific example, Crohn's disease is diagnosed using one or more cytokines selected from the group consisting of RANTES, sIL-6R, sTNFRII, where the ROC area exceeds 0.8.

According to one aspect of the invention, a pair-wise profile of two cytokines is used as a marker for IBDs. According to another embodiment of the invention, the cytokines are selected so that the multi-analyte ROC area exceeds, for example, 0.6, 0.7, 0.8 or 0.9. By the way of non-limiting examples, ulcerative colitis and/or Crohn's disease is diagnosed using a pair of cytokines selected from the list consisting of TNFRII/RANTES, TNFRII/IL-6R, IL-6R/RANTES, IL-5/IL-6R or TNFRII/IL-4, where the ROC area exceeds 0.8. In certain embodiments, both statistically weighted difference analysis and ROC analysis are used to identify diagnostically valuable cytokines of this invention.

Figure 3:
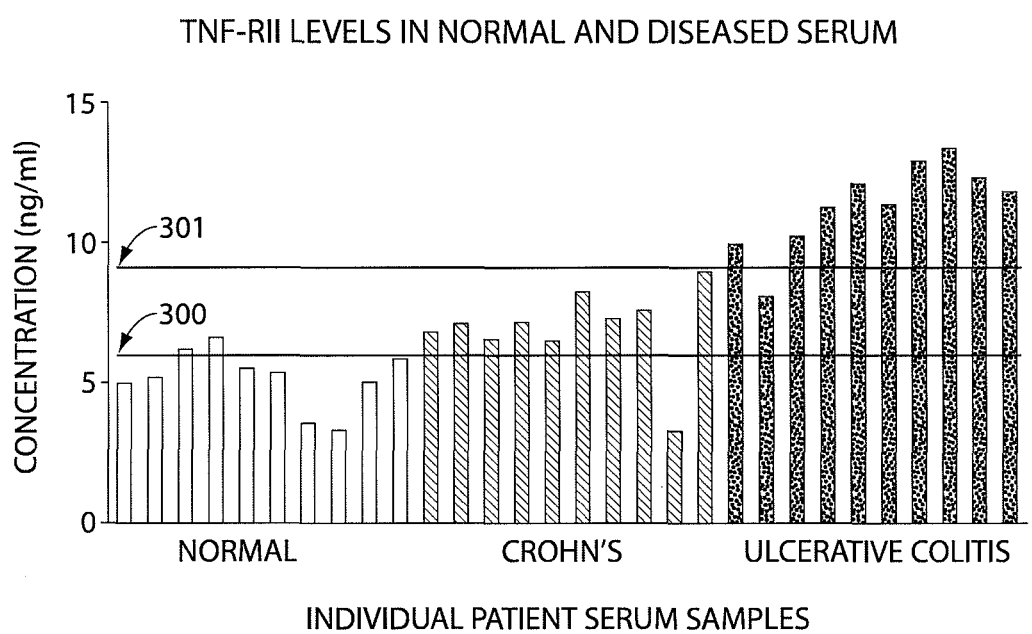
FIG. 3 depicts sTNFRII levels (ng/mL, y axis) in serum for healthy individuals, individuals diagnosed with Crohn's disease and individuals diagnosed with ulcerative colitis.

In certain embodiments of the invention, sTNFRII is determined to be useful as a marker for IBDs for certain methods of the invention. In one embodiment, sTNFRII is used as a marker for Crohn's disease (CD) and ulcerative colitis (UC). FIG. 3 shows that normal and IBD (UC or CD) populations can be distinguished based on the circulating levels of sTNFRII as measured in blood/serum or plasma samples. As determined according to the invention, measurement of sTNFRII levels may be used to diagnose IBD, monitor the progression of disease or the effectiveness of therapy in a patient having IBD, and/or assess the effectiveness of drugs or drug candidates targeting IBDs. Consequently, one embodiment of the invention is a method for diagnosing inflammatory bowel disease comprising: measuring the level of sTNFRII in a sample, for example, a sample obtained from a patient suspected of having inflammatory bowel disease; and diagnosing from the level of sTNFRII the presence or absence in the patient of inflammatory bowel disease. Furthermore, the method may comprise an additional step of administering to the tested patient an effective amount of drug for effective treatment for an IBD.

Another embodiment of the invention involves an assay method comprising: measuring the level of sTNFRII in a sample, for example, a sample obtained from a patient suspected of having inflammatory bowel disease; and determining from the level of sTNFRII the extent of inflammation due to the IBD.

Yet another embodiment is a method for specifically diagnosing ulcerative colitis comprising: measuring the level of sTNFRII in a sample, for example, a sample obtained from a patient suspected of having UC; and diagnosing from the level of sTNFRII the presence or absence in the patient of ulcerative colitis.

Yet another embodiment is a method for monitoring the progression or treatment of IBDs comprising: measuring the levels of sTNFRII in the samples, for example, the samples obtained at different times from a patient that has or is suspected to have an IBD; and determining from the level of sTNFRII the progression or efficacy of treatment of the disease.

Yet another embodiment is a method for evaluation of the effectiveness of a drug or drug candidate for treating IBDs comprising: exposing a human or non-human animal with IBD, or a model system, such as a tissue, a cell culture or a biochemical system, to the drug or drug candidate; measuring the levels of sTNFRII in a sample, for example, a sample obtained from the human or non-human animal or a model system; and determining from the level the effectiveness of the drug or drug candidate. The human or non-human animal in these drug evaluation methods may be replaced with an in vitro IBD model system, for example, tissue, cell culture or biochemical systems that model the behavior of IBDs.

According to one embodiment, the determination if the patient has inflammatory bowel disease from the level of sTNFRII may comprise comparing the level of sTNFRII to a detection cut-off value (see, e.g., cut-off value 300 in FIG. 3). In the example shown in FIG. 3, a sTNFRII level above the detection cut-off value is considered indicative of inflammatory bowel disease. The detection cut-off value is determined from evaluation of the TNFRII levels in patients diagnosed with IBD as compared to healthy individuals. The cut-off value 300 is determined by visually evaluating test data in FIG. 3. A skilled artisan can readily determine an appropriate cut-off value from the data, either visually, or according to other available techniques, for example as described in Boyd J. C. "Reference Limits in the Clinical Laboratory" in *Professional Practice in Clinical Chemistry: A Companion Text*; D. R. Dufour Ed., 1999, Washington D.C.: American Assoc. Clin. Chem., Chapter 2, pp. 2-1 to 2-7, incorporated, herein, by this reference. For background on the selection of decision limits (i.e., cut-offs) or the calculation, from test results, of disease likelihood see Boyd J. C. "Statistical Aids for Test Interpretation" in *Professional Practice in Clinical Chemistry: A Companion Text*; D. R. Dufour Ed., 1999, Washington D.C.: American Assoc. Clin. Chem., Chapter 3, pp. 3-1 to 3-11, U.S. patent application Ser. No. 10/410,572, "System and Method for Identifying a Panel of Indicators," filed on Apr. 8, 2002, published as U.S. Pat. Publ. No. 20040121350, U.S. patent application Ser. No. 10/331,127, "Method and System for Disease Detection Using Marker Combinations," filed on Dec. 27, 2002, published as U.S. Pat. Publ. No. 20040126767, U.S. patent application Ser. No. 10/603,891, "Markers for Differential Diagnosis And Methods of Use Thereof," filed on Jun. 23, 2003, published as U.S. Pat. Publ. No. 20040253637, all of which are incorporated, herein, by this reference.

According to another aspect of the invention, a system for identifying a panel of markers for diagnosis of a disease or a condition includes means for calculating a panel response for each patient in a set of diseased patients and in a set of non-diseased patients. In one embodiment the panel response is a function of a value of each of a plurality of markers in a panel of markers. The means for calculating may be a central processing unit (CPU), as may be available on a desktop computer, a laptop computer, a workstation or a mainframe, for example.

In a preferred embodiment, one or more 'derived markers', which are a function of one or more measured markers, may be incorporated into the set of markers being studied. For example, derived markers may be related to the change in one or more measured marker values, or may be related to a ratio of two measured marker values. In many diseases there will be rapid change in marker value some time after an event. For example, following an acute myocardial infarction, (AMI), myoglobin may rise rapidly and peak about 3 hours from the event. It may then decay back to its nominal value. Looking for changes in markers can be powerful diagnostic tool. Thus, the change in myoglobin over a period of an hour, for example, may be used as a "marker" in the panel.

The sTNFRII levels, in the context of FIG. 3, refers to the concentration of the analyte as measured in a specific assay setting (in this case, measurement on a SECTOR™ Imager 6000 reader (Meso Scale Discovery, a division of Meso Scale Diagnostics, LLC, Gaithersburg, Md.) using kits for multiplexed measurements of cytokines (Meso Scale Diagnostics, LLC, Gaithersburg, Md.). The exact values of the measured levels and associated cut-off values may vary somewhat depending the exact assay conditions and the standards used for assay calibration and natural variation between population groups, however, the general trends (e.g., relationship between the level of the sTNFRII and the disease state) should hold for different assays kits and assay instruments. One of ordinary skill in the art will be able to determine cut-off values applicable for a specific set of assay conditions.

Within the confines of the experimental conditions used to generate the data in FIG. 3 and set forth in the Examples below, the detection cut-off value for sTNFRII (300) is between 5 and 7 ng/ml—determined by visually examining data in FIG. 3. Given the teachings of the present invention and the knowledge of those of ordinary skill in the art, a skilled artisan will readily recognize that the detection cut-off value also determines the selection stringency. The higher the cut-off value selected, the lower is the chance that a false positive diagnosis, i.e., diagnosing a healthy individual with an IBD, but the higher is a chance of a false negative diagnosis, i.e., the chance of not detecting an IBD, and vice versa. Thus, in one embodiment of the invention a plurality of detection cut-off values could be determined to yield varying degrees of diagnostic confidence, e.g., definite diseased state, probable diseased state, low probability disease state, etc. . . .

Given the teachings of the present invention and the knowledge of those of ordinary skill in the art, the cut-off value could be selected by an individual performing the inventive methods, equipment manufacturer or a standard setting organization, for example, FDA by visually analyzing data or with the assistance of the methods of statistical analysis readily available to a skilled artisan, as described above.

In one embodiment, the invention also relates to methods that distinguish ulcerative colitis from Crohn's disease by comparing a cytokine level, e.g. a sTNFRII level to a cytokine cut-off value, e.g. a sTNFRII discrimination cut-off value (see, e.g., cut-off value 301 in FIG. 3), determined according to the invention to distinguish ulcerative colitis from Crohn's disease. In the example shown in FIG. 3, a sTNFRII level above the sTNFRII discrimination cut-off value (301) is considered indicative of ulcerative colitis. A sTNFRII level below the sTNFRII discrimination cut-off value (301) but above the pre-determined detection cut-off value (300) is considered indicative of Crohn's disease.

Within the confines of the instrumentation and experimentation conditions used to generate the data in FIG. 3, the discrimination cut-off value for sTNFRII is between 8 and 10 ng/ml, as determined by visual examination of data in FIG. 3. Selection of a plurality of discrimination cut-off values allows adjustment in stringency of discrimination. The higher the discrimination cut-off value selected, the lower is the chance that a false positive diagnosis, i.e., diagnosing UC in a healthy individual or an individual having CD, but the higher is a chance of a false negative diagnosis, i.e., the chance of not diagnosing UC, and vice versa. When the detection cut-off value is set at the discrimination cut-off value, the methods of the invention detect only patients having ulcerative colitis.

According to certain embodiments, the methods of the present invention are also well suited for measuring plurality of analytes that may be present in a sample, thus, under some circumstances providing improved confidence of detection and discrimination of the diseases. Methods of the present invention are also well suited for measuring plurality of analytes in blood, serum or plasma samples of a patient.

In one embodiment, the invention relates to a method for diagnosing inflammatory bowel disease comprising: measuring the level of a first cytokine, wherein, for example, the sample is obtained from a patient suspected of having inflammatory bowel disease; measuring the level of one or more additional cytokines in the same sample or a different sample from the patient, wherein the one or more additional cytokines are different form the first cytokine; and diagnosing from the first cytokine level and from the one or more additional cytokine levels the presence or absence in said patient of inflammatory bowel disease. In one embodiment, the sample is a serum, plasma or blood sample. In another embodiment, the sample is a fecal or urine sample. Cytokines that may be measured in the methods of the invention include, but are not limited to, cytokines linked to TH1 response, cytokines linked to TH2 response, pro-inflammatory cytokines and/or cytokines selected from the group consisting of IL-1β, IL-12p70, IL-10, IL-2, GM-CSF, TNF, IL-8, IL-4, IL-5, IL-6, Eotaxin, IFN-α, IFN-γ, sIL-6R, IL-12(total), IL-13, MIP-1β, MCP-1, RANTES and sTNFRII. In one embodiment, the cytokines are selected from the group consisting of IL-12p70, IL-10, IL-2, TNF, IL-8, IL-4, IL-5, IL-6, Eotaxin, sIL-6R, IL-12(total), MIP-1β, MCP-1, RANTES and sTNFRII. In another embodiment, the cytokines are selected from the group consisting of Eotaxin, sIL-6R, MIP-1β, MCP-1, and RANTES. In one embodiment, the first cytokine is MCP-1 and the additional cytokine is MIP-1β. In another embodiment, the first cytokine is sTNFRII. In one specific example of this embodiment, the additional cytokine(s) are selected from the group consisting of IL-12p70, IL-10, IL-2, TNF, IL-8, IL-4, IL-5, IL-6, Eotaxin, sIL-6R, IL-12(total), MIP-1β, MCP-1 and RANTES. In another specific example, the additional cytokine(s) are selected from the group consisting of Eotaxin, sIL-6R, MIP-1β, MCP-1, and RANTES. In another specific example, the additional cytokine(s) are selected from the group consisting of sIL-6R and RANTES. In another specific example, the additional cytokine is MIP-1β. In another embodiment, the first cytokine is sTNFRII and the additional cytokine is IL-4.

The cytokine measurements may also be used to determine the extent of inflammation due to IBD by comparing the levels of one or more cytokines in the patient diagnosed with an IBD to a cytokine level profile for healthy individuals, or by comparing the levels of one or more cytokines in the patient diagnosed with an IBD, where the samples are collected at different times. Thus, the assay methods are particularly advantageous for patient monitoring, treatment monitoring, or evaluation of the effectiveness of a drug or drug candidate.

In one embodiment of the invention, sTNFRII is selected as the first cytokine. The determining step may comprise comparing the measured levels of sTNFRII and one or more additional cytokines to a cytokine profile determined to be indicative of inflammatory bowel disease. The profile can be created for a combination of analytes using measurements of cytokine levels in diseased individuals as compared to healthy individuals. The profile may be a pair-wise correlation profile or a multivariable correlation profile. Examples of the pair-wise correlation profiles include, but not limited to, profiles exemplified by FIGS. 4-16.

Figure 4:
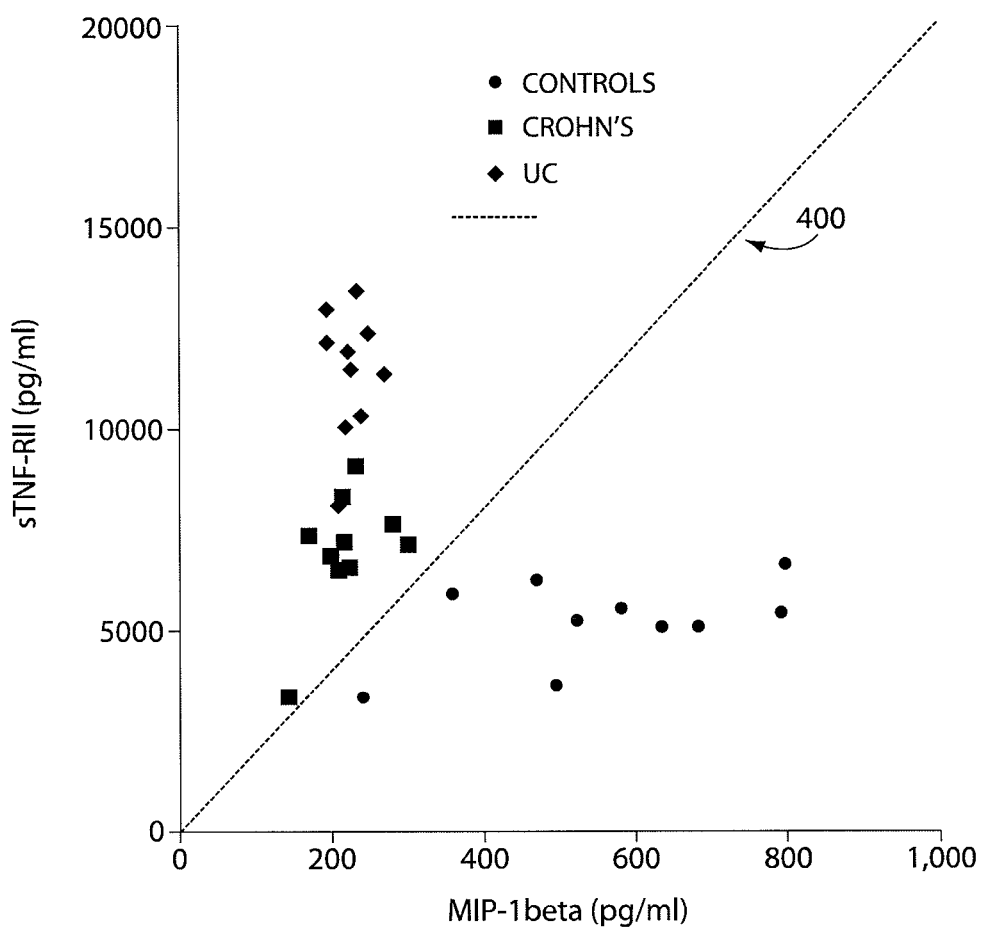
FIG. 4 depicts profiles of sTNFRII levels (pg/mL, y axis) and MIP-1β levels (pg/mL, x axis) in serum for healthy individuals, individuals diagnosed with Crohn's disease and individuals diagnosed with ulcerative colitis.
Figure 5:
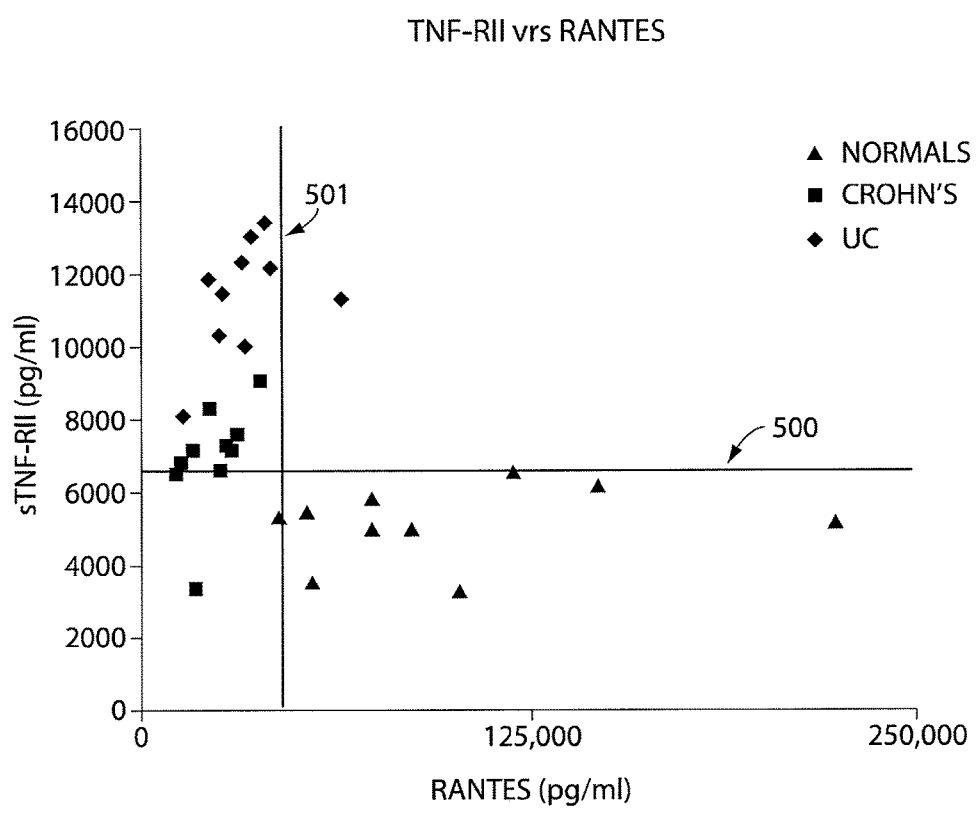
FIG. 5 depicts profiles of sTNFRII levels (pg/mL, y axis) and RANTES levels (pg/mL, x axis) in serum for healthy individuals, individuals diagnosed with Crohn's disease and individuals diagnosed with ulcerative colitis.
Figure 6:
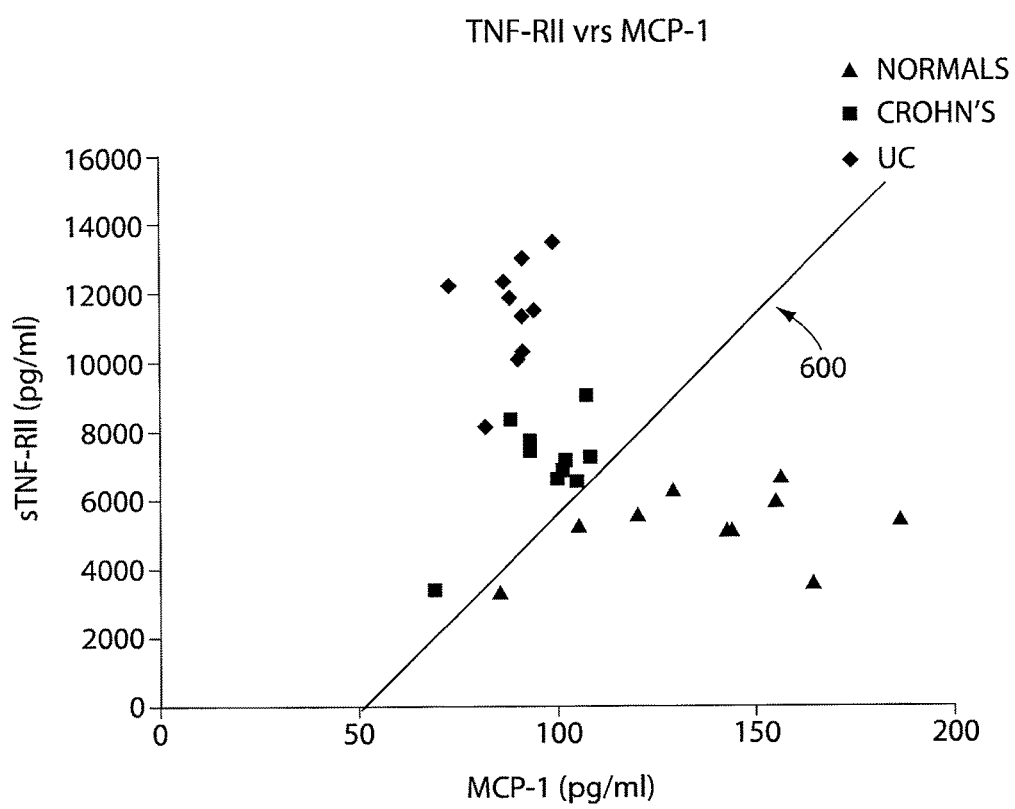
FIG. 6 depicts profiles of sTNFRII levels (pg/mL, y axis) and MCP-1 levels (pg/mL, x axis) in serum for healthy individuals, individuals diagnosed with Crohn's disease and individuals diagnosed with ulcerative colitis.
Figure 9:
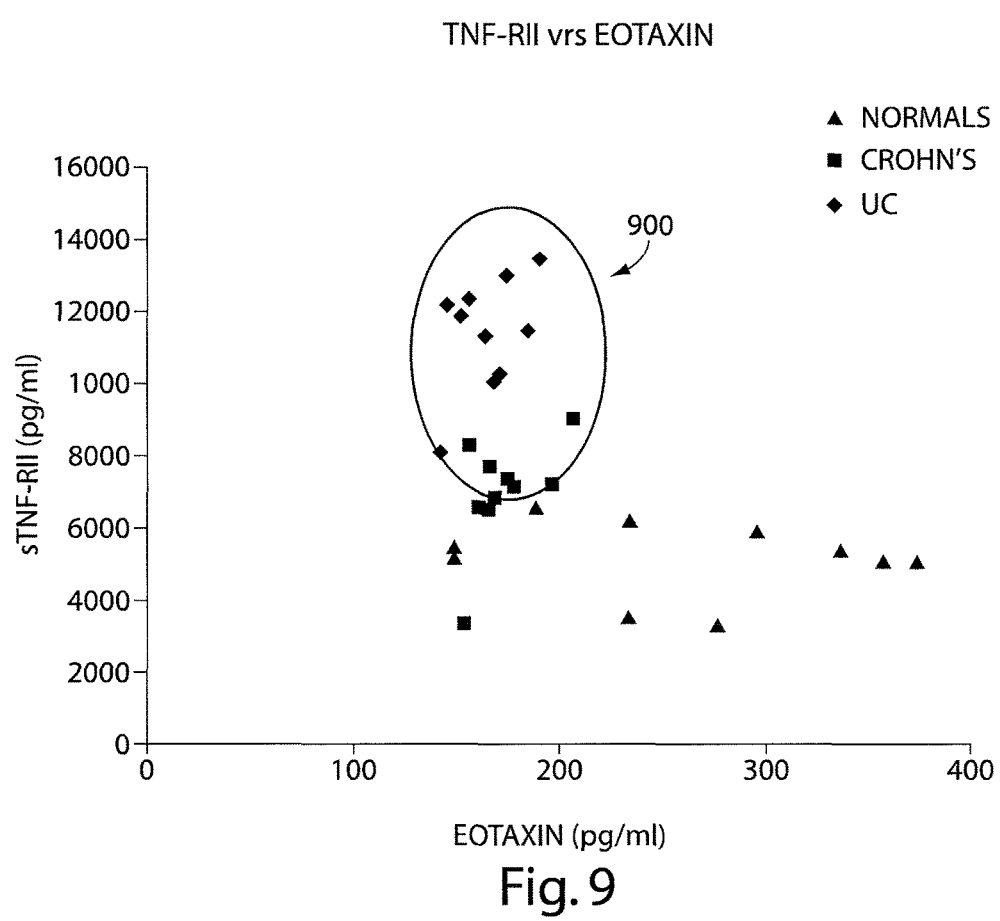
FIG. 9 depicts profiles of sTNFRII levels (pg/mL, y axis) and Eotaxin levels (pg/mL, x axis) in serum for healthy individuals, individuals diagnosed with Crohn's disease and individuals diagnosed with ulcerative colitis.
Figure 10:
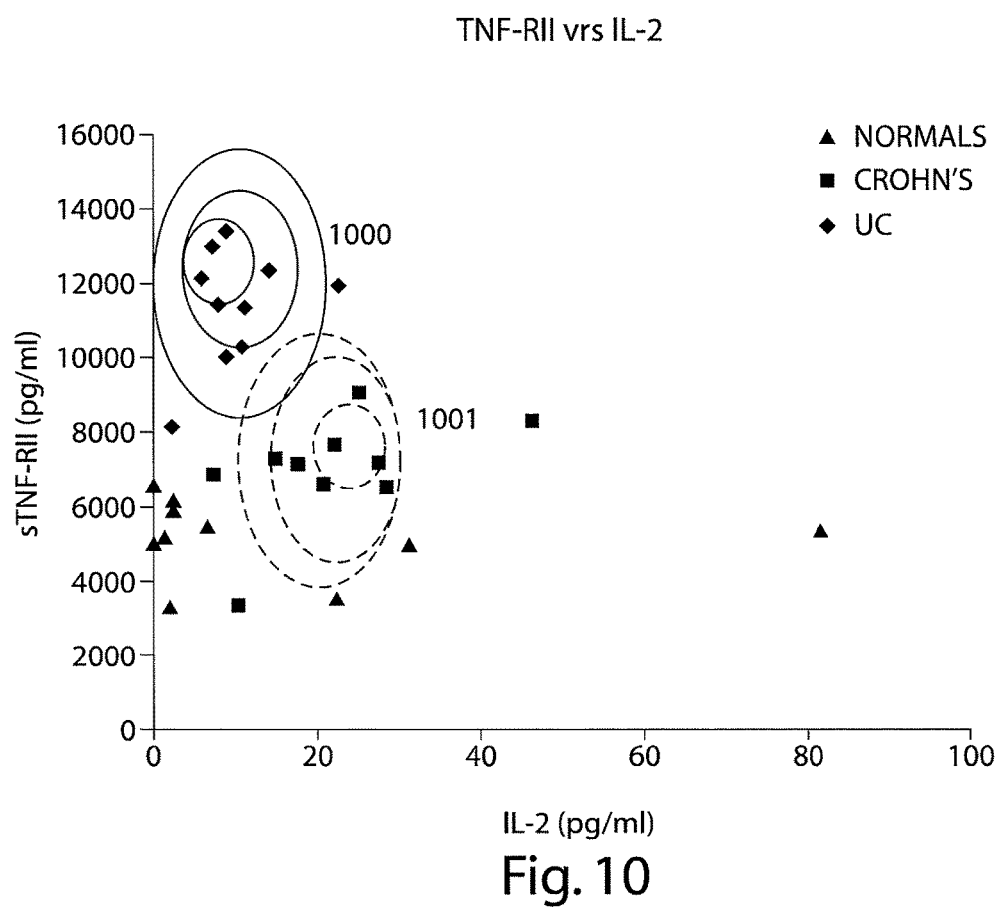
FIG. 10 depicts profiles of sTNFRII levels (pg/mL, y axis) and IL-2 levels (pg/mL, x axis) in serum for healthy individuals, individuals diagnosed with Crohn's disease and individuals diagnosed with ulcerative colitis.

In some cases, ratios of the levels of two analytes can be used to diagnose disease and/or discriminate between diseases. FIG. 4 shows the correlation of serum sTNRFII and MIP-1β for normal and diseased populations and shows that a ratio of the sTNFRII level to the MIP-1β level above a detection cut-off ratio value (i.e., the slope of line 400 through the origin) is indicative of the inflammatory bowel disease. The cut-off ratio value was selected by visual examination of data in FIG. 4, however, a skilled artisan can readily understand that the cut-off ratio value could also be selected using methods of statistical analysis known in the art. Alternatively, a curve (e.g., a line) in a plot showing the correlation of two analytes can be used for diagnosis and/or discrimination. FIG. 6 shows the correlation of serum levels sTNRFII and MCP-1 and shows that a sample that gives a point in the correlation plot with a sTNFRII level above a sTNFRII detection cut-off line (600, in this specific example, drawn by visual examination of data) is indicative in inflammatory bowel disease. Similarly, cut-off surfaces can be defined in 3 or more dimensional multi-analyte correlations. Combinations of cut-off values, lines or other curves (or surfaces) and/or ratios can be used to improve diagnosis. FIG. 5 shows a correlation of sTNFRII and RANTES levels and shows that the combination of a sTNFRII level above a TNFRII detection cut-off value (500) and RANTES level below a detection cut-off value (501) is indicative of inflammatory bowel disease. In certain embodiments, values for multiple cytokine levels are analyzed to determine if they fall within pre-determined detection zones in a correlation plot, the detection zones being areas (in 2-D plots) or volumes (in higher dimensional plots) that are indicative of a disease state. FIG. 9 shows a correlation of sTNFRII and Eotaxin levels and shows that levels of the two cytokines that fall within a detection zone 900 are indicative of inflammatory bowel disease.

According to one embodiment of the invention, the assay methods may further distinguish ulcerative colitis from Crohn's disease on the basis of a measured sTNFRII level and one or more additional measured cytokine levels. Ulcerative colitis may be distinguished from Crohn's disease by comparing measured levels to profiles indicative of Crohn's disease or ulcerative colitis. By way of example, FIG. 4 is a correlation plot that shows a clear separation of normal, UC and CD populations.

Figure 7:
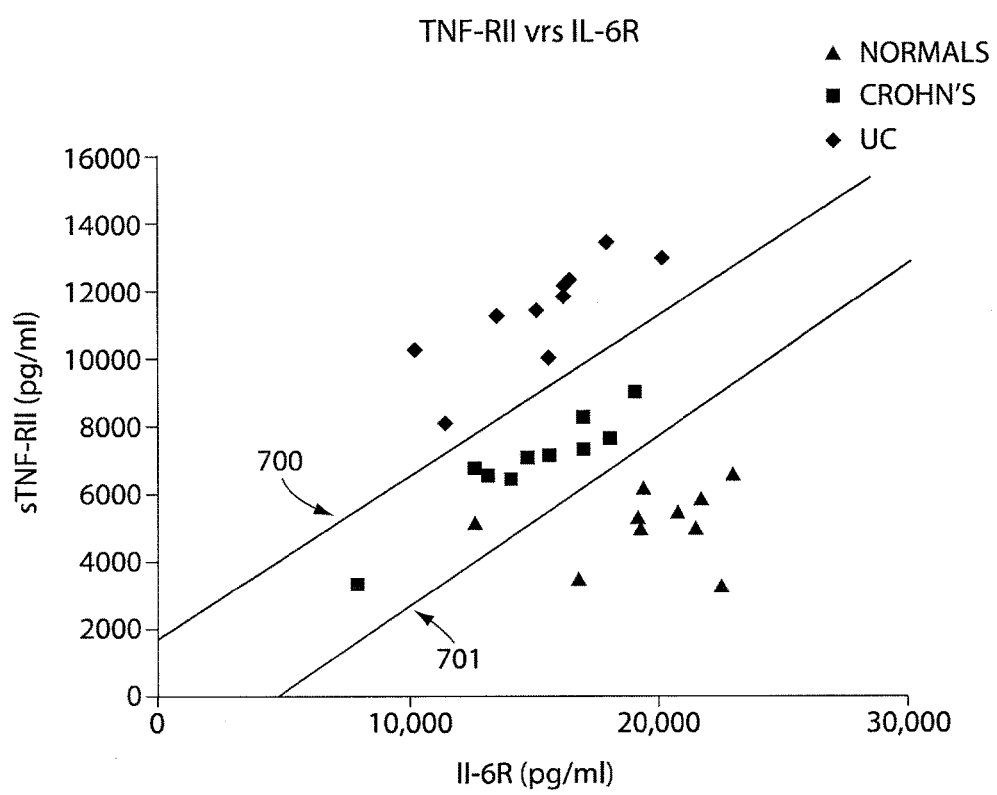
FIG. 7 depicts profiles of sTNFRII levels (pg/mL, y axis) and sIL-6R levels (pg/mL, x axis) in serum for healthy individuals, individuals diagnosed with Crohn's disease and individuals diagnosed with ulcerative colitis.
Figure 8:
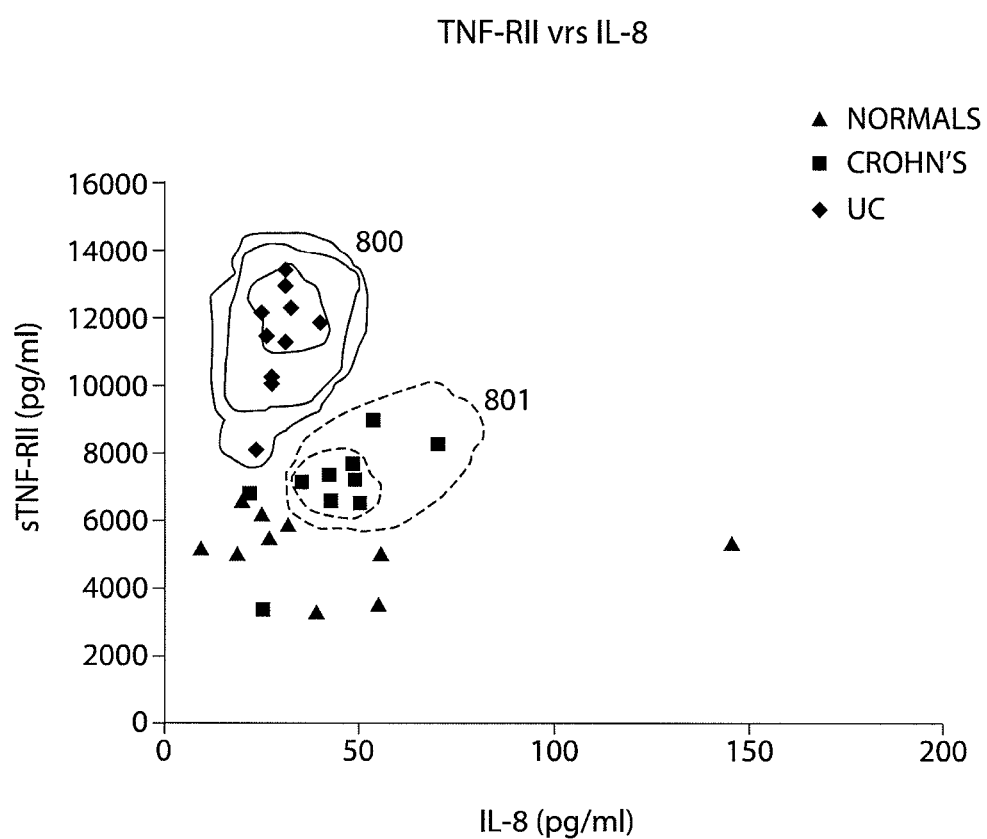
FIG. 8 depicts profiles of sTNFRII levels (pg/mL, y axis) and IL-8 levels (pg/mL, x axis) in serum for healthy individuals, individuals diagnosed with Crohn's disease and individuals diagnosed with ulcerative colitis.
Figure 15:
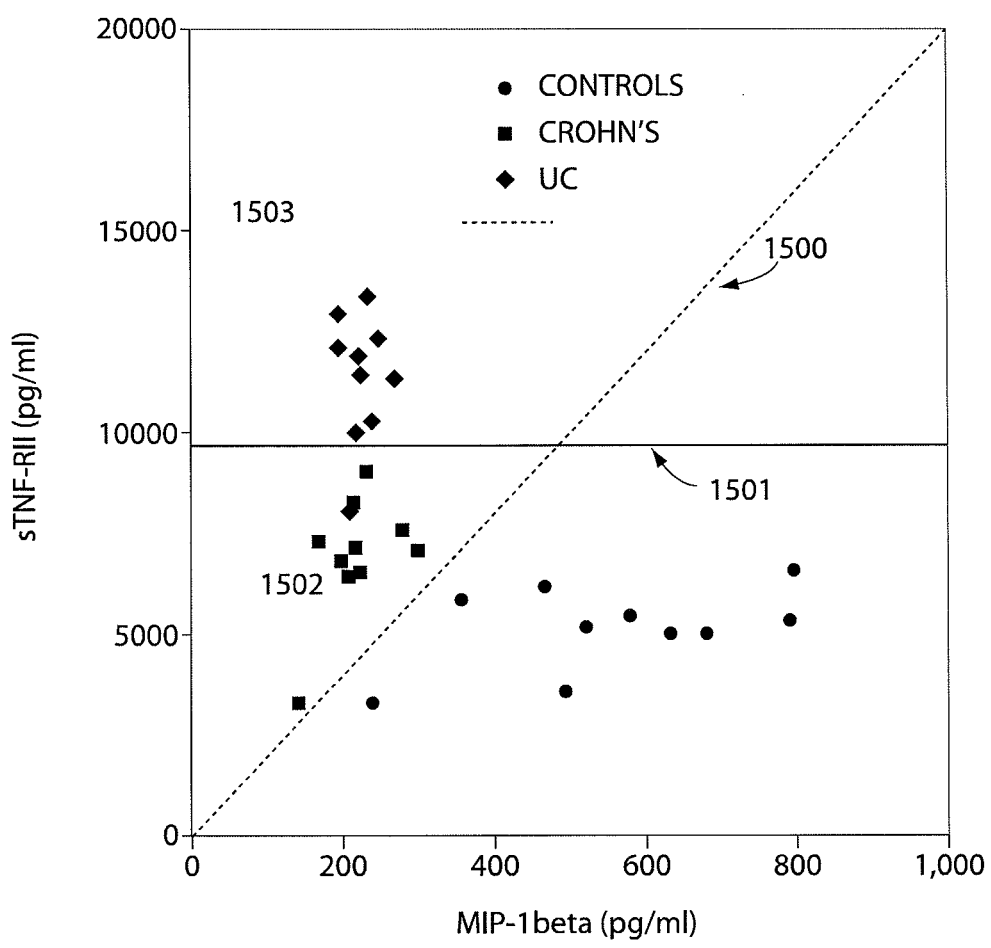
FIG. 15 depicts profiles of sTNFRII levels (pg/ml, y axis) and MIP-1β levels (pg/ml, x axis) in serum for healthy individuals, individuals diagnosed with Crohn's disease and individuals diagnosed with ulcerative colitis.
Figure 16:
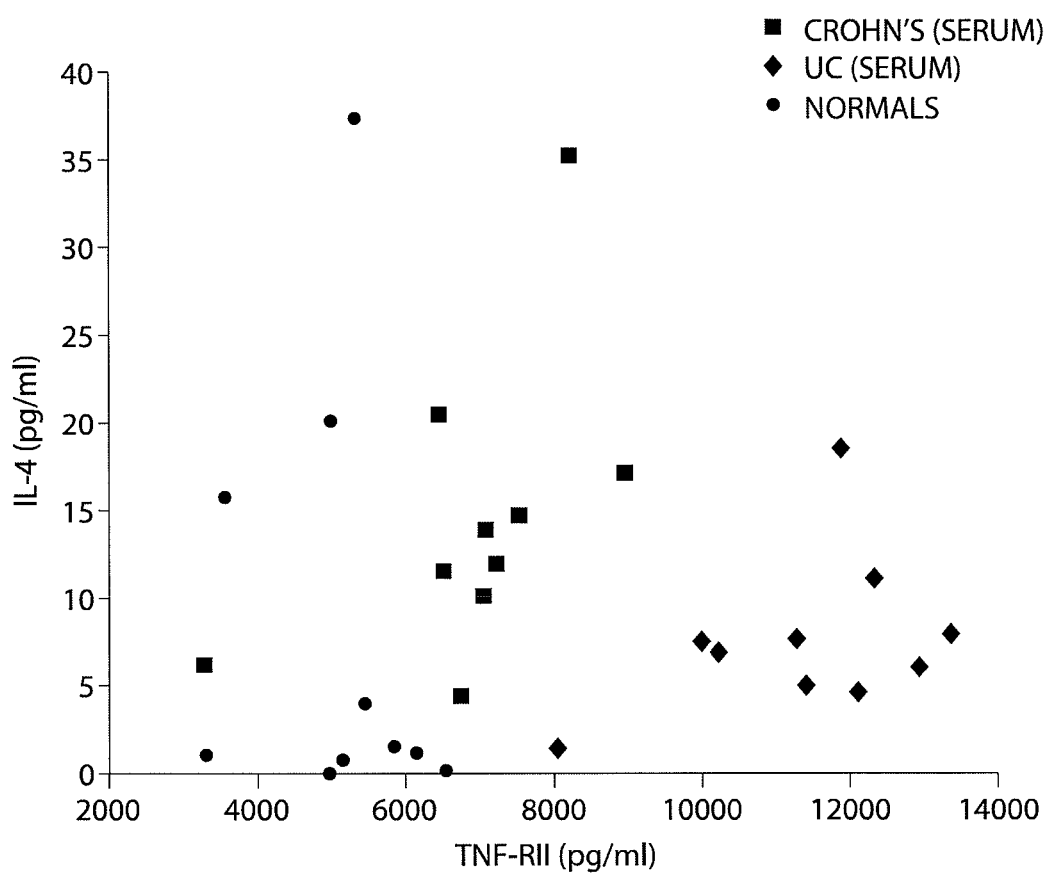
FIG. 16 depicts profiles of sTNFRII levels (pg/ml, x axis) and IL-4 levels (pg/ml, y axis) in serum for healthy individuals, individuals diagnosed with Crohn's disease and individuals diagnosed with ulcerative colitis.

Discrimination can be achieved through discrimination cut-off values, lines, ratios and/or zones indicative of Crohn's disease or ulcerative colitis. FIG. 7 shows the correlation of sTNFRII with sIL-6R and shows that sTNFRII levels that lie above discrimination cut-off line 700 are indicative of UC, while sTNFRII levels that lie between discrimination cut-off line 700 and detection cut-off line 701 are indicative of CD, and sTNFRII levels that fall below detection cut-off line 701 are indicative of normal subjects. FIG. 15 shows a correlation plot for sTNFRII and MIP-1β and shows that the UC and CD populations fall predominantly into areas 1502 and 1503, respectively, defined by a first detection cut-off line 1500 and a second discrimination cut-off line 1501 on the correlation plot.

Comparison of measured cytokine values to cytokine profiles may be used to not only provide yes-no answers but also to predict the probability of disease or the confidence in a measurement, for example as discussed above for ROC area analysis. For example, multiple cut-off values, ratios, lines, zones, etc. can be defined that provide different levels of statistical confidence to a diagnostic conclusion. By way of example, FIGS. 8 and 10 have disease specific zones 800, 801, 1000 and 1001 that are shown as contours, the different contour levels providing different degrees of sensitivity and specificity. The contour level may be selected to correspond to the probability of the disease and/or confidence level of diagnostics. The contours in FIGS. 8 and 10 were defined visually, but a skilled artisan will readily recognize that the counters on a contour plot could be defined by using one of the above discussed methods of statistical analysis.

Figure 11:
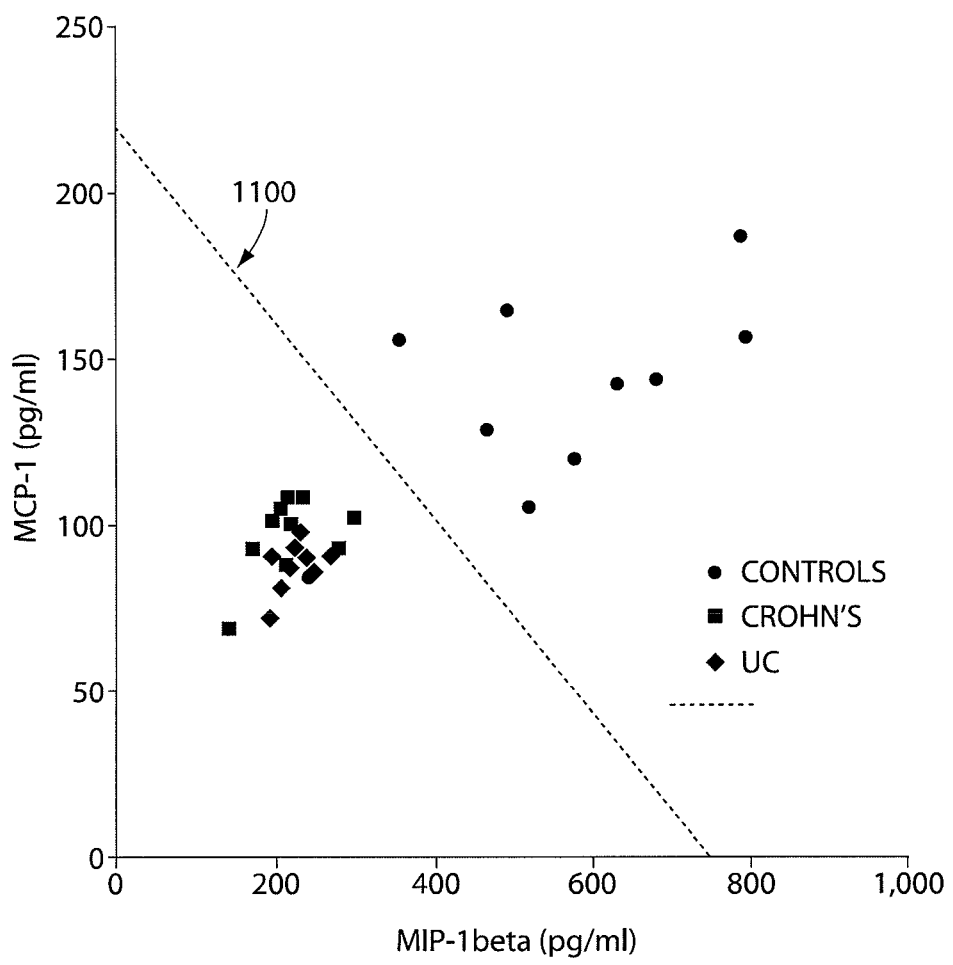
FIG. 11 depicts profiles of MCP-1 levels (pg/ml, y axis) and MIP-1β levels (pg/ml, x axis) in serum for healthy individuals, individuals diagnosed with Crohn's disease and individuals diagnosed with ulcerative colitis.
Figure 12:
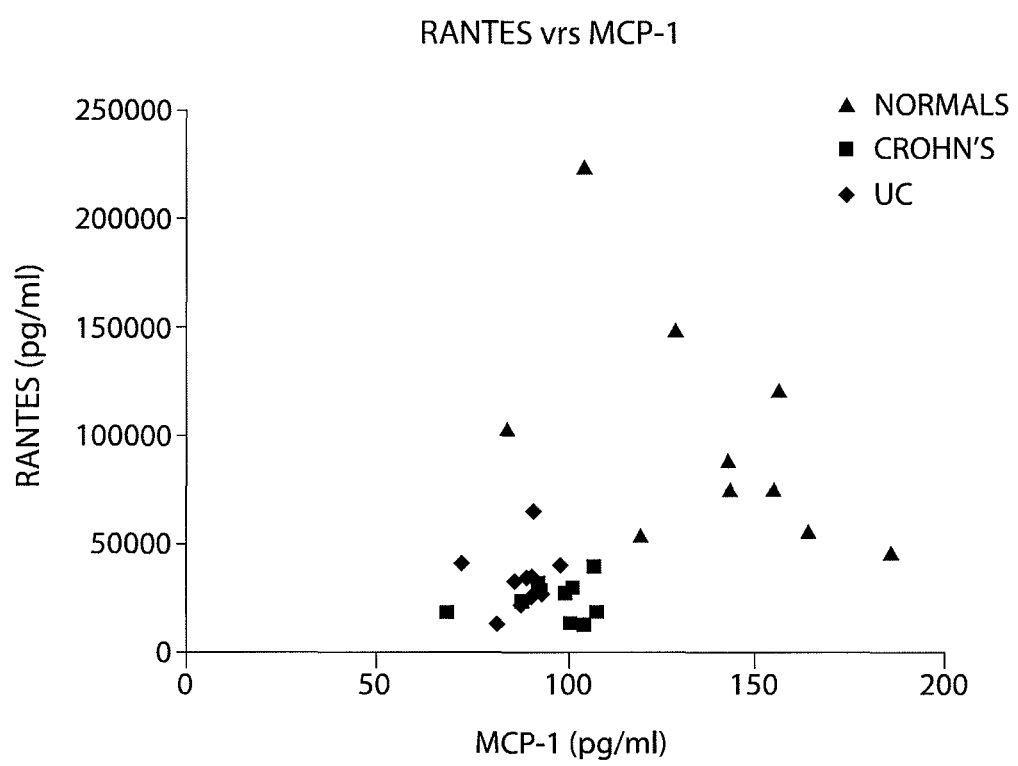
FIG. 12 depicts profiles of RANTES levels (pg/mL, y axis) and MCP-1 levels (pg/mL, x axis) in serum for healthy individuals, individuals diagnosed with Crohn's disease and individuals diagnosed with ulcerative colitis.
Figure 13:
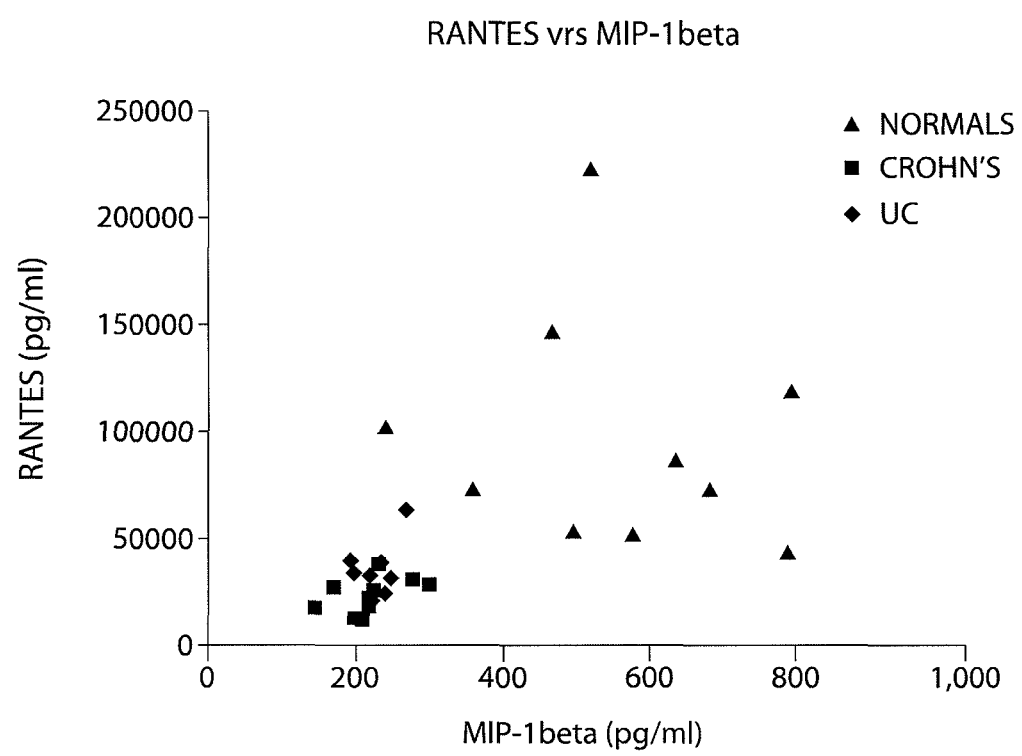
FIG. 13 depicts profiles of RANTES levels (pg/mL, y axis) and MIP-1β levels (pg/mL, x axis) in serum for healthy individuals, individuals diagnosed with Crohn's disease and individuals diagnosed with ulcerative colitis.
Figure 14:
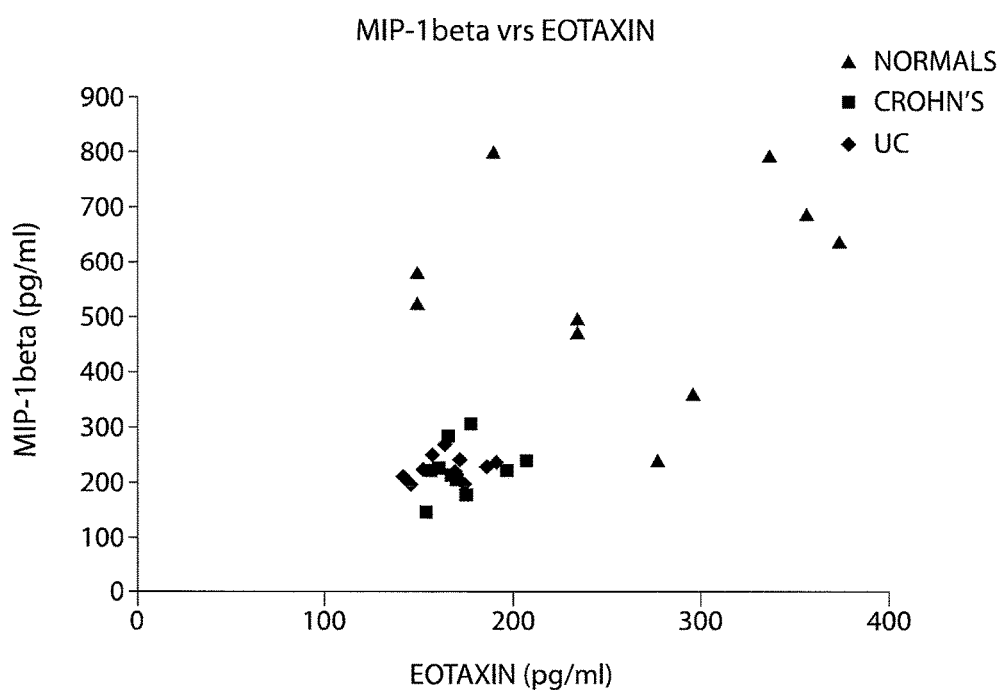
FIG. 14 depicts profiles of MIP-1β levels (pg/mL, y axis) and Eotaxin levels (pg/mL, x axis) in serum for healthy individuals, individuals diagnosed with Crohn's disease and individuals diagnosed with ulcerative colitis.

Certain embodiments of the invention that are applicable to methods for determining if the patient has inflammatory bowel disease and distinguishing various IBDs may also comprise comparing the levels of a first cytokine selected from the group consisting of sTNFRII, IL-1β, IL-12p70, IL-10, IL-2, GM-CSF, TNF, IL-8, IL-4, IL-5, IL-6, Eotaxin, IFN-α, IFN-γ, sIL-6R, IL-12(total), IL-13, MIP-1β, MCP-1 and RANTES and one or more additional cytokines selected from the same group to a cytokine profile indicative of the inflammatory bowel disease. In one embodiment, the cytokines are selected from the group consisting of sTNFRII, Eotaxin, sIL-6R, MIP-1β, MCP-1, and RANTES. In another embodiment, the first cytokine is MCP-1 and the additional cytokine is MIP-1β. In another embodiment, the first cytokine is sTNFRII and the additional cytokine is IL-4. The profile can be created for a specific combination of analytes by measuring cytokine levels in diseased individuals and in healthy individuals. Examples of the profiles include, but not limited to, profiles exemplified by FIGS. 11-16. FIG. 11 shows one example where individual cytokines measurements do not completely distinguish between normal and diseased populations (because of overlap in the distributions), but use or two cytokines provides a cut-off line that provides excellent to separation of the populations.

One of ordinary skill in the art of diagnostic assays and statistical analysis of data, given the teaching and guidance provided herein, will be able to select without undue burden appropriate cut-off values, lines, ratios, zones etc. for best meeting the needs (e.g., sensitivity and specificity) for a particular application. A variety of statistical tools, such as, for example, receiver operating characteristic (ROC) curves, are available for evaluating the effect of adjustments to cut-offs on assay performance (e.g., predicted true positive fraction, false positive fraction, true negative fraction and false negative fraction). Alternatively, statistical analysis of patient populations can allow conversion of specific analyte values into probabilities that the patient has or does not have a disease. For background on the selection and analysis of populations of individuals so as to determine reference ranges see Boyd J. C. "Reference Limits in the Clinical Laboratory" in *Professional Practice in Clinical Chemistry: A Companion Text*; D. R. Dufour Ed., 1999, Washington D.C.: American Assoc. Clin. Chem., Chapter 2, pp. 2-1 to 2-7. For background on the selection of decision limits (i.e., cut-offs) or the calculation, from test results, of disease likelihood see Boyd J. C. "Statistical Aids for Test Interpretation" in *Professional Practice in Clinical Chemistry: A Companion Text*; D. R. Dufour Ed., 1999, Washington D.C.: American Assoc. Clin. Chem., Chapter 3, pp. 3-1 to 3-11.

Given the teachings of the present invention, a skilled artisan will also recognize that the choice of first cytokine and one or more additional cytokines may transpose correlation plot axes and consequently the criteria for determining whether measured cytokine levels of a patient's samples falling above or below particular cut-off ratios, lines and/or profiles is indicative of a disease state and will be able to adjust the analysis accordingly.

The cytokine levels may be measured using any of a number of techniques available to the person of ordinary skill in the art, e.g., direct physical measurements (e.g., mass spectrometry) or binding assays (e.g., immunoassays, agglutination assays, and immunochromatographic assays). The method may also comprise measuring a signal that results from a chemical reaction, e.g., a change in optical absorbance, a change in fluorescence, the generation of chemiluminescence or electrochemiluminescence, a change in reflectivity, refractive index or light scattering, the accumulation or release of detectable labels from the surface, the oxidation or reduction or redox species, an electrical current or potential, changes in magnetic fields, etc. Suitable detection techniques may detect binding events by measuring the participation of labeled binding reagents through the measurement of the labels via their photoluminescence (e.g., via measurement of fluorescence, time-resolved fluorescence, evanescent wave fluorescence, up-converting phosphors, multi-photon fluorescence, etc.), chemiluminescence, electrochemiluminescence, light scattering, optical absorbance, radioactivity, magnetic fields, enzymatic activity (e.g., by measuring enzyme activity through enzymatic reactions that cause changes in optical absorbance or fluorescence or cause the emission of chemiluminescence). Alternatively, detection techniques may be used that do not require the use of labels, e.g., techniques based on measuring mass (e.g., surface acoustic wave measurements), refractive index (e.g., surface plasmon resonance measurements), or the inherent luminescence of an analyte.

Binding assays for measuring cytokine levels may use solid phase or homogenous formats. Suitable assay methods include sandwich or competitive binding assays. Examples of sandwich immunoassays are described in U.S. Pat. No. 4,168,146 to Grubb et al. and U.S. Pat. No. 4,366,241 to Tom et al., both of which are incorporated herein by reference. Examples of competitive immunoassays include those disclosed in U.S. Pat. No. 4,235,601 to Deutsch et al., U.S. Pat. No. 4,442,204 to Liotta, and U.S. Pat. No. 5,208,535 to Buechler et al., all of which are incorporated herein by reference.

Multiple cytokines may be measured using a multiplexed assay format, e.g., multiplexing through the use of binding reagent arrays, multiplexing using spectral discrimination of labels, multiplexing by flow cytometric analysis of binding assays carried out on particles (e.g., using the Luminex system). Suitable multiplexing methods include array based binding assays using patterned arrays of immobilized antibodies directed against the cytokines of interest. Various approaches for conducting multiplexed assays have been described. For example, multiplexed testing is described in U.S. patent application Ser. Nos. 10/185,274 and 10/185,363, both filed on Jun. 28, 2002, entitled "Assay Plates, Reader Systems and Methods For Luminescence Test Measurements," published as U.S. Pat. Publ. No. 20040022677 and US20050052646, respectively, U.S. patent application Ser. No. 10/238,960, filed Sep. 10, 2002, entitled "Methods, Reagents, Kits and Apparatus for Protein Function," published as U.S. Pat. Publ. No. 20030207290, U.S. patent application Ser. No. 10/238,391, filed Sep. 10, 2002, entitled "Methods and apparatus for conducting multiple measurements on a sample"; published as U.S. Pat. Publ. No. 20030113713, U.S. patent application Ser. No. 10/980,198, filed on Nov. 3, 2004, entitled "Modular Assay Plates, Reader System and Methods For Test Measurements," published as U.S. Pat. Publ. No. 20050142033; and U.S. patent application Ser. No. 10/744,726, filed on Dec. 23, 2003, entitled "Assay Cartridges and Methods of Using Same," published as U.S. Pat. Publ. No. 20040189311, each of which is incorporated by this reference. One approach to multiplexing binding assays involves the use of patterned arrays of binding reagents (see, e.g., U.S. Pat. Nos. 5,807,522 and 6,110,426, both entitled "Methods for Fabricating Microarrays of Biological Samples" issued Sep. 15, 1998 and Aug. 29, 2000 respectively), Delehanty J B, Printing functional protein microarrays using piezoelectric capillaries, *Methods Mol Biol*. (2004) 278:135-44; Lue R Y, Chen G Y, Zhu Q, Lesaicherre M L, Yao S Q, Site-specific immobilization of biotinylated proteins for protein microarray analysis, *Methods Mol Biol*. (2004) 278:85-100; Lovett, Toxicogenomics: Toxicologists Brace for Genomics Revolution, *Science* (2000) 289: 536-537; Berns A., Cancer: Gene expression in diagnosis, *Nature* (2000) 403, 491-492; Walt, Molecular Biology: Bead-based Fiber-Optic Arrays, *Science* (2000) 287: 451-452 for more details). Another approach involves the use of binding reagents coated on beads that can be individually identified and interrogated. International Patent publication WO9926067A1 (Watkins et al.) describes the use of magnetic particles that vary in size to assay multiple analytes; particles belonging to different distinct size ranges are used to assay different analytes. The particles are designed to be distinguished and individually interrogated by flow cytometry. Vignali has described a multiplex binding assay in which 64 different bead sets of microparticles are employed, each having a uniform and distinct proportion of two dyes (Vignali, D. A. A., "Multiplexed Particle-Based Flow Cytometric Assays," *J. Immu-* nol. Meth. (2000) 243:243-255). A similar approach involving a set of 15 different beads of differing size and fluorescence has been disclosed as useful for simultaneous typing of multiple pneumococcal serotypes (Park, M. K. et al., "A Latex Bead-Based Flow Cytometric Immunoassay Capable Of Simultaneous Typing Of Multiple Pneumococcal Serotypes (Multibead Assay)," *Clin Diagn Lab Immunol.* (2000) 7:486-9). Bishop, J. E. et al. have described a multiplex sandwich assay for simultaneous quantification of six human cytokines (Bishop, J. E. et al., "Simultaneous Quantification of Six Human Cytokines in a Single Sample Using Microparticle-based Flow Cytometric Technology," *Clin Chem.* (1999) 45:1693-1694).

Advantageously, in certain embodiments, tests may be conducted on a single sample including, but not limited to, blood, serum, plasma, hair, sweat, urine, feces, tissue, biopsies, saliva, skin, mucosa, CNS fluid, bone marrow, tissue extracts, cells, cell extracts, cell culture supernatants, and lymphatic fluids. Particularly advantageous are blood, blood serum, blood plasma, fecal matter, biopsy tissue, intestinal mucosa and urine. Specifically advantageous are blood, blood serum, blood plasma, fecal and urine samples due to the easy and non-surgically invasive collection techniques.

A diagnostic test may also be is conducted in a single assay chamber, such as a single well of an assay plate or an assay chamber that is an assay chamber of a cartridge. The assay modules (for example assay plates or cartridges, or multi-well assay plates), methods and apparatuses for conducting assay measurements suitable for the present invention are described, for example, in U.S. patent application Ser. Nos. 10/185,274 and 10/185,363, both filed on Jun. 28, 2002, entitled "Assay Plates, Reader Systems and Methods For Luminescence Test Measurements," published as U.S. Pat. Publ. No. 20040022677 and US20050052646, respectively, U.S. patent application Ser. No. 10/980,198, filed on Nov. 3, 2004, entitled "Modular Assay Plates, Reader System and Methods For Test Measurements," published as U.S. Pat. Publ. No. 20050142033, and U.S. patent application Ser. No. 10/744,726, filed on Dec. 23, 2003, entitled "Assay Cartridges and Methods of Using Same," published as U.S. Pat. Publ. No. 20040189311, each of which is incorporated by this reference. Assay plates and plate readers are now commercially available (MULTI-SPOT® and MULTI-ARRAY™ plates and SECTOR™ instruments, Meso Scale Discovery, a division of Meso Scale Diagnostics, LLC, Gaithersburg, Md.).

Various diagnostic tests of the present invention may be further supplemented with a diagnostic test to determine if the patient has viral or bacterial infection. Thus, in certain embodiments, the invention further comprises determining if the patient has viral or bacterial infection. Various diagnostic tests of the present invention may be further supplemented with visual patient observation by the doctor, radiological testing and/or histological testing of the patient. The methods of the invention may further comprise administering to the tested patient an effective amount of drug for effective treatment of the diagnosed IBD.

The function and advantage of these and other embodiments of the present invention may be more fully understood from the examples below. The following examples, while illustrative of certain embodiments of the invention, do not exemplify the full scope of the invention.

EXAMPLES

The following examples are illustrative of some of the methods and instrumentation falling within the scope of the present invention. They are, of course, not to be considered in any way limitative of the invention. Numerous changes and modifications can be made with respect to the invention by one of ordinary skill in the art without undue experimentation.

Materials & Methods:

Multi-Well Plates for Electrochemiluminescence Measurements:

Electrochemiluminescence measurements were carried out using multi-well plates having integrated carbon ink electrodes (MULTI-SPOT® plates from Meso Scale Discovery, a division of Meso Scale Diagnostics, LLC.). A dielectric layer patterned over the working electrode in each well exposed ten regions or "spots" on the working electrode. The basic detection technology is described in U.S. patent application Ser. Nos. 10/185,274 and 10/185,363, both filed on Jun. 28, 2002, entitled "Assay Plates, Reader Systems and Methods For Luminescence Test Measurements," published as U.S. Pat. Publ. No. 20040022677 and US20050052646, respectively. Kits for multiplexed measurements of cytokines using this technology are available from Meso Scale Diagnostics, LLC, Gaithersburg, Md. The kits include plates with an array of capture antibodies on the "spots" of each well. The measurements described herein used two different cytokine kits that each measured a different 10 cytokine panel. The first kit measured IL-1β, IL-12p70, IL-10, IL-2, GM-CSF, TNF-α, IL-8, IL-4, IL-5, and IL-6. The second kit measured Eotaxin, IFN-α, IFN-γ, sIL-6R, IL-12(total), IL-13, MCP-1, MIP-1β, RANTES, and sTNF-RII. The kits also included detection antibodies for each analyte (labeled with MSD Sulfo-TAG, an electrochemiluminescent label), an assay diluent (MSD Serum Cytokine Diluent) and an antibody diluent (MSD Cytokine Antibody Diluent). The labeled antibodies for each panel were mixed and diluted to a concentration of 2.5 ug/ml of each anti body in the antibody diluent.

Sample Preparation

Matched human serum and EDTA plasma samples were obtained from non-diseased individuals and individuals with either Crohn's disease or ulcerative colitis. The patients were diagnosed with either Crohn's or ulcerative colitis according to current medical practice. Diseased patients were not undergoing therapy at the time of sample draw. Non-diseased (normal) individuals were defined as having normal general appearance, height and weight, blood pressure, temperature and skin free of lesions. A detailed questionnaire was also filled out by these individuals, and those displaying any evidence of any current disease were excluded from this normal group.

Samples were diluted 1:50 for the sIL-6R, RANTES, and sTNF-RII measurements. All other cytokines were measured using undiluted samples.

Calibrators

Calibrators containing known concentrations of all cytokines in a given panel were prepared in the assay diluent.

Electrochemiluminescence Measurement Instrument

Electrochemiluminescence was induced and measured in the MULTI-SPOT® plates using a SECTOR™ Imager 6000 (Meso Scale Discovery, a division of Meso Scale Diagnostics, LLC., Gaithersburg, Md.).

Example 1

Cytokine Detection and Determination of Suitability of Cytokines to Act as Diagnostic Markers of IBD Cytokine levels were measured in a multiplexed solid-phase sandwich immunoassay.

The plates were blocked with blocking buffer (200 ul/well of Blocker A, MSD Discovery, a division of Meso Scale Diagnostics, LLC.) for 1 hour at room temperature and then washed with PBS (3×250 ul). Assay diluent (25 ul) was then added to each well and the plate incubated for 30 minutes. Calibrators and serum/plasma samples were then added to the plates (25 ul/well). Each plate contained three replicates of each calibrator (8 levels) and three replicates of each sample. The plates were then incubating with shaking for 2 hours. The mixture of detection antibodies was then added to the plates (10 ul/well) and the plate incubated for another 2 hours with shaking. The plates were then washed with PBS (3×250 ul), MSD Read Buffer T was added (150 ul/well) and the plates read on a Sector 6000 instrument. Cytokine concentration levels were calculated by back-fitting to 4 parameter logistic fits to the calibration curves for each analyte.

Table 2 lists, for each cytokine, one indicator of the utility of the cytokine as a marker for distinguishing between normal and diseased patients using ten patients clinically diagnosed with Crohn's disease, ten patients clinically diagnosed with ulcerative colitis and ten healthy individuals. The utility is presented as a statistically weighted difference between control individuals and diseased patients, calculated as $$\frac{D-N}{\sqrt{\sigma_D * \sigma_N}}$$

where D is the median concentration of a cytokine in patients diagnosed as having ulcerative colitis or Crohn's disease, N is the median of the control individuals, $\sigma_D$ in the standard deviation of D and $\sigma_N$ is the standard deviation of N. The larger the magnitude, the greater the statistical difference between the diseased and normal populations. The measured levels for IL-1β, GM-CSF, IFN-α, IFN-γ and IL-13 were, for the most part, below the detection limits for these assays. The results are plotted in FIGS. 3-16.

TABLE 2

| Analyte | Crohn's | UC |
|---|---|---|
| IL-1β | 0.4 | 1.8 |
| IL-12p70 | 1.0 | 0.4 |
| IL-10 | −0.1 | −0.3 |
| IL-2 | 1.1 | 0.5 |
| TNF | −1.5 | −0.8 |
| IL-8 | 0.7 | 0.0 |
| IL-4 | 1.1 | 0.7 |
| IL-5 | 0.4 | 0.3 |
| IL-6 | 0.4 | 1.1 |
| Eotaxin | −2.3 | −2.4 |
| IFN-γ | 0.2 | 0.7 |
| sIL-6R | −1.6 | −1.4 |
| IL-12(total) | −0.1 | −0.5 |
| MIP-1β | −3.7 | −5.1 |
| MCP-1 | −2.3 | −3.6 |
| RANTES | −2.6 | −1.7 |
| sTNFRII | 1.5 | 5.0 |

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims.

The present invention is directed to each individual feature, system, material and/or method described herein. In addition, any combination of two or more such features, systems, materials and/or methods, provided that such features, systems, materials and/or methods are not mutually inconsistent, is included within the scope of the present invention.

In the claims (as well as in the specification above), all transitional phrases or phrases of inclusion, such as "comprising," "including," "carrying," "having," "containing," "composed of," "made of," "formed of," "involving" and the like shall be interpreted to be open-ended, i.e. to mean "including but not limited to" and, therefore, encompassing the items listed thereafter and equivalents thereof as well as additional items. Only the transitional phrases or phrases of inclusion "consisting of" and to "consisting essentially of" are to be interpreted as closed or semi-closed phrases, respectively. The indefinite articles "a" and "an," as used herein in the specification and in the claims, unless clearly indicated to the contrary, should be understood to mean "at least one."

Various publications are cited herein, the disclosures of which are incorporated by reference in their entireties. In cases where the present specification and a document incorporated by reference and/or referred to herein include conflicting disclosure, and/or inconsistent use of terminology, and/or the incorporated/referenced documents use or define terms differently than they are used or defined in the present specification, the present specification shall control.

What is claimed is:

1. A multiplexed assay kit used to evaluate the efficacy of a treatment regimen in a patient diagnosed with inflammatory bowel disease, said kit comprising:
    (a) a multi-well assay plate comprising a plurality of wells, each well comprising at least four discrete binding domains with capture antibodies to which a plurality of biomarkers are bound, said plurality of biomarkers are selected from the group consisting of soluble Tumor Necrosis Factor receptor II (sTNFRII) and Macrophage Inflammatory Protein-1beta (MIP-1 beta), and at least two additional biomarkers selected from the group consisting of eotaxin, Soluble Interleukin-6 Receptor (sIL-6R), Monocyte Chemoattractant Protein 1 (MCP-1), Regulated on Activation, Normal T cell Expressed and Secreted protein (RANTES), wherein the multi-well assay plate is capable of communicating with a processor, the processor configured to determine a ratio of sTNFRII to MIP-1 beta in samples from said patients versus people not diagnosed with inflammatory bowel disease; and
    (b) in one or more vials, containers, or compartments, a set of labeled detection antibodies specific for said plurality of biomarkers.

2. The kit of claim 1, which is further configured to detect a ratio of sTNFRII to eotaxin in samples from said patients versus people not diagnosed with inflammatory bowel disease.

3. The kit of claim 1 wherein said at least one additional biomarker comprises MCP-1.

4. The kit of claim 1 wherein said kit is configured to measure said level using an immunoassay.

5. The kit of claim 1 further comprising one or more diluents.

6. The kit of claim 1 wherein said detection antibodies are labeled with an electrochemiluminescent label (ECL).

7. The kit of claim 1 wherein said kit further comprises an ECL read buffer.

8. The kit of claim 1 wherein said discrete binding domains are positioned on an electrode within said well.

9. The kit of claim 1 wherein said set of calibrator proteins comprise a liquid formulation of calibrator proteins.

10. The kit of claim 1 wherein said kit further comprises one or more additional assay reagents used in said assay, said one or more additional assay reagents provided in one or more vials, containers, or compartments of said kit.

11. The kit of claim 1, which further contains one or more vials, containers, or compartments comprising a set of calibrator proteins.

12. The kit of claim 11 wherein said set of calibrator proteins comprises a lyophilized blend of proteins.

13. An assay system, comprising the kit of claim 1 and an electrochemiluminescent plate reader.

14. An assay system, comprising the kit of claim 11 and an electrochemiluminescent plate reader.

15. The kit of claim 1, which comprises capture antibodies to at least two additional biomarkers selected from the group consisting of eotaxin, sIL-6R, MCP-1, and RANTES.

16. The kit of claim 1, which is further configured to detect a ratio of sTNFRII to sIL-6R in samples from said patients versus people not diagnosed with inflammatory bowel disease.

17. The kit of claim 1, which is further configured to detect a ratio of MIP-1beta to MCP-1 in samples from said patients versus people not diagnosed with inflammatory bowel disease.

18. The kit of claim 1, which is further configured to detect a ratio of RANTES to MCP-1 in samples from said patients versus people not diagnosed with inflammatory bowel disease.

19. The kit of claim 1, wherein the samples from said patients are selected from the group consisting of blood, serum, plasma, fecal, urine and combinations thereof.

* * * * *